(12) United States Patent
Boland et al.

(10) Patent No.: US 10,285,932 B2
(45) Date of Patent: May 14, 2019

(54) SKIN CARE FORMULATIONS

(71) Applicant: Colorescience, Inc., Carlsbad, CA (US)

(72) Inventors: Patricia McGill Boland, Houston, TX (US); Deborah Eileen Gregg Bouche, Houston, TX (US); John Anthony Garruto, Encinitas, CA (US); Bethany Ann McCarver, Oceanside, CA (US)

(73) Assignee: COLORESCIENCE, INC., Carlsbad, CA (US)

( * ) Notice: Subject to any disclaimer, the term of this patent is extended or adjusted under 35 U.S.C. 154(b) by 24 days.

(21) Appl. No.: 15/965,205

(22) Filed: Apr. 27, 2018

(65) Prior Publication Data

US 2018/0243206 A1 Aug. 30, 2018

Related U.S. Application Data

(63) Continuation-in-part of application No. 14/735,778, filed on Jun. 10, 2015, now Pat. No. 9,956,163.

(60) Provisional application No. 62/011,472, filed on Jun. 12, 2014, provisional application No. 62/538,390, filed on Jul. 28, 2017.

(51) Int. Cl.
| | |
|---|---|
| *A61K 8/9789* | (2017.01) |
| *A61K 8/9722* | (2017.01) |
| *A61K 8/9711* | (2017.01) |
| *A61K 8/9717* | (2017.01) |
| *A61K 8/73* | (2006.01) |
| *A61K 8/41* | (2006.01) |
| *A61Q 19/02* | (2006.01) |
| *A61K 8/9728* | (2017.01) |
| *A61K 8/60* | (2006.01) |
| *A61Q 19/08* | (2006.01) |

(52) U.S. Cl.
CPC ............ *A61K 8/9789* (2017.08); *A61K 8/416* (2013.01); *A61K 8/602* (2013.01); *A61K 8/733* (2013.01); *A61K 8/9711* (2017.08); *A61K 8/9717* (2017.08); *A61K 8/9722* (2017.08); *A61K 8/9728* (2017.08); *A61Q 19/02* (2013.01); *A61Q 19/08* (2013.01); *A61K 2800/30* (2013.01)

(58) Field of Classification Search
None
See application file for complete search history.

(56) References Cited

U.S. PATENT DOCUMENTS

2010/0129305 A1* 5/2010 Lee ........................ A61K 8/31
424/63

FOREIGN PATENT DOCUMENTS

| JP | 2009196969 A | * | 9/2009 | | |
|---|---|---|---|---|---|
| JP | 2009242296 A | * | 10/2009 | | |
| WO | WO-2007078056 A1 | * | 7/2007 | ............ | A61Q 19/00 |
| WO | WO-2013046137 A2 | * | 4/2013 | ............ | A61Q 19/08 |
| WO | WO-2013049599 A2 | * | 4/2013 | ............... | A61Q 1/00 |

OTHER PUBLICATIONS

Remington's Pharmaceutical Sciences 100 years. 17 Ed. "Dilution and Concentration". p. 19. (Year: 1985).*
Tremellahyaluronicacid—WSK .Version 4: 2005. [Retrieved from the internet on: Jun. 6, 2018]. Retrieved from: <URL: http://www.in-cosmetics.com/_novadocuments/4871>. (Year: 2005).*
"acne.org". Retrieved from the Internet on: Jun. 7, 2018. Retrieved from: <URL: https://www.acne.org/messageboard/topic/319656-the-good-list-non-comedogenic-ingredients-and-products/>. (Year: 2012).*

* cited by examiner

*Primary Examiner* — Amy L Clark
(74) *Attorney, Agent, or Firm* — Knobbe, Martens, Olson & Bear LLP

(57) ABSTRACT

Formulations to treat skin discoloration via a multi-modal approach are provided in some embodiments in which select ingredients work together to effectively brighten skin and treat hyperpigmentation. In other embodiments, soothing redness correction formulations are provided. In yet other embodiments, certain formulations are renewal formulations adapted to treat the eye area to, for example, reduce laxity, puffiness, wrinkles and/or dark circles around the eye.

18 Claims, No Drawings

SKIN CARE FORMULATIONS

This application is a continuation-in-part of Ser. No. 14/735,778 filed on Jun. 10, 2015, which claims priority to U.S. Provisional Application No. 62/011,472, filed on Jun. 12, 2014; this application also claims priority to 62/538,390, filed on Jul. 28, 2017; which are all hereby incorporated by reference.

BACKGROUND

The field of the invention relates generally to skin care. According to several embodiments, topical formulations that show visible beneficial dermatological results are provided.

Skin care formulations, such as those for the eye and face, include for example, serums, lotions, and creams, are used for various purposes. Formulations can act as a moisturizer, provide coverage, or contain vitamins. For protection, some formulations contain a sun protection factor (SPF).

SUMMARY

Despite the large number of cosmetic formulations for treating the eye that are on the market, there remains a need for an enhanced topical formulation that simultaneously reduces and corrects the appearance of dark circles, puffiness, fine lines, and wrinkles, provides hydration, and addresses the delicate needs of the eye area (which can be much more sensitive than other skin on the face). In one embodiment, the formulation provides significant UV protection (such as physical UVA and UVB sun protection), In several embodiments, a 3-in-1 renewal formulation is provided that advantageously delivers both immediate and long-term results. For example, a topical formulation according to several embodiments (i) immediately brightens the eye area and corrects imperfections to reduce dark circles and puffiness for a refreshed and rested appearance, (ii) provides a chemical-free, 100% mineral sunscreen to defend against UVA/UVB rays and environmental stressors that contribute to skin aging, and (iii) restores skin health with hydration that provides support for sagging skin to enhance the eye area.

One benefit of the formulations described herein is the ability for a user to apply a formulation to achieve correction, hydration and protection in a single product rather than using multiple products. Use of a single product around the eye area is advantageous in several embodiments because application of multiple products around the eye can increase the risk of irritating the delicate eye area (based on, for example, adverse interactions of the various products, the mere act of physically touching the eye area multiple times, layering of multiple products resulting in lack of breathability or poor absorption, etc.).

Because of the delicate eye area, there is a particular need in one embodiment for an enhanced formulation that is both efficacious and suitable for delicate skin, and additionally incorporates a broad-spectrum sunscreen, without being irritating or chalky. In several embodiments, the formulations described herein comprise a sun protection factor of SPF 35 or higher. In one embodiment, mineral (chemical-free) sunscreen ingredients are provided as a defense against photoaging. In several embodiments, zinc oxide is used as a sunscreen. In some embodiments, titanium dioxide is used. In other embodiments, a combination of zinc oxide and titanium dioxide is used. In one embodiment, a clear formulation is provided in which titanium dioxide, zinc oxide and colorants are not included.

In several embodiments, the invention comprises or consists essentially of a unique topical formulation that comprises at least 3, 4, 5, 6 or all of the following (with ranges provided as % m/m, % m/v, % w/w, % w/v or % v/v of the formulation):

(i) A combination of sea water and marine microalgae (such as seaweed, brown seaweed extract, algin) that protects skin from impurities while addressing skin laxity and under-eye bags by helping support the health of collagen and increasing skin firmness. In some embodiments, these ingredients are provided in a range of about 0.01-5%, and ranges in between (e.g., 0.05-3%).

(ii) At least two polysaccharides that maintain the health of capillaries to minimize puffiness around the eyes and reduce pigmentation that causes dark circles. The polysaccharides include, but are not limited to, an *Ascophyllum* polysaccharide (such as *Ascophyllum nodosum*), an *Asparagopsis* polysaccharide (such as *Asparagopsis armata*), and polysaccharides isolated from other seaweed and algae. In some embodiments, these ingredients are provided in a range of about 0.01-5%, and ranges in between (e.g., 0.05-3%).

(iii) Plant-based water-retention agent and betaine for hydration, overall suppleness of skin and maintaining water balance over time. The plant-based water-retention agent can serve as an alternative to hyaluronic acid and includes, but is not limited to, *Tremella* (such as *Tremella fuciformis* sporocarp). Other extractions from mushrooms and fungus may also be used as a source of water-retaining agents and/or polysaccharides. In some embodiments, these ingredients are provided in a range of about 0.01-5%, and ranges in between (e.g., 0.05-3%).

(iv) At least two plant extracts working synergistically to reduce the volume and depth of fine lines, wrinkles, and/or crow's feet, minimize the fold of the upper eyelid for a smoother appearance, and/or correct discoloration to fade dark circles. These ingredients include, but are not limited to, *Albizia* (such as *Albizia Julibrissin*) and darutoside. In some embodiments, the darutoside is extracted from the *Siegesbeckia Orientalis* plant. In some embodiments, a *Centella* extract is included, such as an *asiaticoside* extracted from *Centella asiatica*. In some embodiments, these ingredients are provided in a range of about 0.01-5%, and ranges in between (e.g., 0.05-3%).

(v) Peptides, vitamins and other ingredients to address such concerns as under-eye bags, dark circles, fine lines, wrinkles, and puffiness. These ingredients include, but are not limited to, palmitoyl tripeptide-5, panthenol, *Dunaliella* (such as *Dunaliella salina*), and sodium hyaluronate. In some embodiments, these ingredients are provided in a range of about 0.01-8%, and ranges in between (e.g., 0.05-4%).

(vi) Optionally, in some embodiments, one or more of the following is provided: solvents, binders, viscosity balancing agents, pH adjustors, colorants, surfactants, and skin conditioning agents. In some embodiments, these ingredients are provided in a range of about 20-80%. Optionally, preservatives and fragrances may be included in non-irritating amounts (e.g., less than 1, 2 or 5%, such as 0.01-4%, and ranges in between).

(vii) Optionally, in some embodiments, agents to provide an SPF of at least 15 (e.g., 15, 25, 35, 50, or higher). These ingredients include, but are not limited to zinc oxide and titanium dioxide. In some embodiments, these ingredients are provided in a range of about 2-20%, and ranges in between (e.g., 4-12%). These SPF agents are excluded in a formulation that may be clear and does not contain zinc oxide or titanium dioxide.

In one embodiment, at least 80% or 90% of the ingredients in (i)-(vii) are provided % m/m or % w/w. In several embodiments, effective (e.g., therapeutic) amounts of ingredients are included in the formulation. An effective (e.g., therapeutic) amount, in one embodiment, may be that which reduces the appearances of fine lines, puffiness, dark circles, and/or laxity after at least four weeks of twice daily use.

In some embodiments, the invention comprises a topical formulation with an SPF of at least 15 (e.g., 15, 25, 35, 50, or higher) that comprises at least four (and in one embodiment all) of the following: titanium dioxide, zinc oxide, *Albizia*, darutoside, *Dunaliella*, algin, *Ascophyllum, Asparagopsism*, betaine, and *Tremella* (including for example extracts, components or portions thereof), as well as other ingredients. In some embodiments, the darutoside is extracted from the *Siegesbeckia Orientalis* plant. In some embodiments, a *Centella* extract is included, such as an *asiaticoside* extracted from *Centella asiatica*.

In some embodiments, the invention comprises a topical formulation without titanium dioxide or zinc oxide as SPF factors, wherein the formulation comprises at least four (and in one embodiment all) of the following: *Albizia*, darutoside, *Dunaliella*, algin, *Ascophyllum, Asparagopsism*, betaine, and *Tremella* (including for example extracts, components or portions thereof), as well as other ingredients. In some embodiments, the darutoside is extracted from the *Siegesbeckia Orientalis* plant. In some embodiments, a *Centella* extract is included, such as an *asiaticoside* extracted from *Centella asiatica*.

In several embodiments, a topical formulation is provided that comprises water, sorbitol, *Ascophyllum nodosum* extract, *Asparagopsis armata* extract, palmitoyl tripeptide-5, panthenol, sodium hyaluronate, *Dunaliella salina* extract, hydrolyzed algin, sucrose, glycerin, *Albizia julibrissin* bark extract, darutoside, *Tremella fuciformis* sporocarp (silver ear mushroom) extract, betaine, xanthan gum, polysorbate 20, phenoxyethanol, ethylhexylglycerin, caprylyl glycol, and caprylhydroxamic acid.

In some embodiments, the formulation comprises at least four (and in one embodiment all) of the following: titanium dioxide, zinc oxide, *Albizia julibrissin, Dunaliella salina*, hydrolyzed algin, betaine, *Ascophyllum nodosum, Asparagopsis armata, Centella asiatica, Siegesbeckia Orientalis* and *Tremella fuciformis* sporocarp (including for example extracts, components or portions thereof), as well as other ingredients. Such other ingredients include, but are not limited to, one or more of: water, siloxanes, triglycerides, dimethicone, glycerin, panthenol, jojoba esters, sodium hyaluronate, palmitoyltripeptide-5, pantolactone, and tocopherol. In one embodiment, neither titanium dioxide nor zinc oxide is included.

In some embodiments, several of the ingredients work synergistically. The synergism achieves a beneficial result that is more efficacious than the additive effects of the ingredients, according to some embodiments.

Many embodiments achieve at least one of the following benefits (and in some embodiments, all of the benefits): (i) immediately brightens and corrects dark circles (e.g., by providing a neutral peach tone), (ii) reduces puffiness (e.g., through use of a cooling applicator), (iii) smooths fine lines and wrinkles, (iii) protects against future sun damage, (iv) hydrates, and (v) primes skin for smooth application of eye makeup.

In some embodiments, the treated skin is re-hydrated, in which hydration is increased by 25-75% or more post treatment with the formulations described herein (within minutes or hours post treatment). In some embodiments, the appearance of wrinkles, dark circles, fine lines and/or laxity is reduced by at least 25-95% post treatment with the formulation used consistently (e.g., 1, 2 or 3 times daily) after, for example, 7, 14, 21, 28, 60 or 90 days.

In some embodiments, the formulations provided herein are concentrated and provided in a mask form to be left on the skin for at least 5, 15, 30, or 60 minutes (or as an overnight repair mask). Gentle cleansers may also include many of the ingredients of the formulations described herein and may additionally include witch hazel or other gentle toners (for toner-type cleansers) or foaming ingredients (for washes and foaming cleansers). In several embodiments, more concentrated formulations are provided for use as a spot treatment or for treatment of an area smaller than the area treated by a mask.

In some embodiments, visible reductions in the appearance of dark circles and puffiness may be observed within minutes of use of a formulation as described herein, due to, for example, a color correction pigment and/or the anti-inflammatory activity of the ingredients. A soothing or cooling sensation may be experienced by the user upon application to the skin, which may also contribute to the reduced puffiness.

In several embodiments, an SPF of least 30 (e.g., 35, 50) is used while avoiding a chalky appearance and allowing eye makeup to be applied smoothly over the treated area. This is advantageous because certain sunscreens can discolor the skin and/or provide an unsuitable surface for application of other cosmetics.

In several embodiments, the formulation is provided as a topical formulation, including but not limited to a mineral-based formulation. In several embodiments, the formulation is provided in the form of a liquid, cream, serum, or gel.

The areas of the eye to be treated include, for example, the entire orbital region, from under eye to brow, including eyelids. Although the formulations described herein are useful to treat the eye area, in some embodiments the formulations can also be used to treat other skin regions that would benefit from brightening, reduced puffiness, smoothing of fine lines and wrinkles, hydration and sun protection. For example, the nasolabial folds and marionette lines may be particularly well suited to benefit from the formulations described herein. Scars may be treated in some embodiments.

In several embodiments, the formulation is contained within an applicator with a dispensing tip. The applicator may have a metallic tip in some embodiments. The applicator may be pen or cylindrical shaped in one embodiment and the tip may be a round or oval partially flattened or curved shape to help application to the contours of the eye and other areas. For eye applications, the tip may be narrow and contoured to navigate the contours of the eye region. Larger applicators may be used for other regions on the face and body. In several embodiments, the formulation is used during or after a dermatological procedure (including but not limited to brow lifts, blepharoplasty, botulin and other neurotoxins, facials, fillers, dermabrasion, microdermabrasion, micro-needling, peels, exfoliations, suctioning, fluid delivery, acid treatments, massage, extractions, energy-based and other treatments, such as lasers, thermal, radiofrequency, light (e.g., photofacials/IPL), etc.). In some embodiments, the applicator includes fluid delivery conduits, pressure/air-based devices, and sonicators. In several embodiments, formulations may be stored and/or delivered by use of a bottle and/or dropper. In several embodiments, the dropper or other delivery device is graduated and/or indexed to deliver pre-set amounts of a formulation disclosed herein. In some embodiments, the applicator includes a paddle or contoured metallic tip to facilitate application.

In some embodiments, the formulation is contained within an applicator having a tip with a thermal conductivity configured to provide a cooling effect. In several embodiments, the invention comprises a use or method of reducing laxity, puffiness, wrinkles and/or dark circles around the eye, comprising administration, or instructing administration of a formula described herein. A kit is provided in some embodiments, wherein the kit is configured for reducing laxity, puffiness, wrinkles and/or dark circles around the eye and includes a formulation as described herein, wherein the formulation is contained within an applicator having a metallic cooling tip.

In some embodiments, formulations for treating hyperpigmentation and/or lightening skin regions, and methods of using same, are provided. In some embodiments the formulation comprises a formulation for treating skin discoloration, comprising or consisting essentially of a *bidens pilosa* extract, an acetyl *rheum rhaponticum* root extract, a Vitamin E compound, a *thermus thermophillus* ferment extract, a zinc oxide; and a titanium dioxide. The formulation provides, in some embodiments, a sun protection factor of SPF 15, 30, 50 or more and is in the form of a liquid (e.g., liquid lotion, liquid serum), cream or gel (e.g., ointment gel). The formulation, in some embodiments, further comprises two or more (e.g., all) of the following an *Elaeis Guineensis* oil, a *Gossypium Herbaceum* seed oil, a *Linum Usitatissimum* seed oil, a *Citrus Paradisi* seed extract, and a *Fusanus Spicatus* wood oil.

In many embodiments, effective amounts of the active ingredients are provided. For example, in one embodiment, these amounts are as follows: *bidens pilosa* extract is provided in a range of 0.005-5%, the acetyl *rheum rhaponticum* root extract is provided in a range of 0.005-5%, the Vitamin E compound is provided in a range of 0.05-5%, the *thermus thermophillus* ferment extract is provided in a range of 0.05-10%, the zinc oxide is provided in a range of 5-15%; and the titanium dioxide in a range of 10-15%, wherein the ranges are provided as % m/m, % m/v, or % v/v of the formulation.

In some embodiments, topical formulations for treating skin discoloration and methods of using same, are provided, comprising (i) a first anti-melanin agent, wherein said first anti-melanin agent comprises a *bidens pilosa* extract, (ii) a second anti-melanin agent, wherein said second anti-melanin agent comprises a *rheum* extract (e.g., *rheum rhaponticum* extract), (iii) an anti-inflammatory agent (e.g., a Vitamin E compound), and (iv) a sun protection agent (e.g., zinc oxide and/or titanium dioxide) with an SPF of 15, 30, 50 or more. An antioxidant (e.g., *thermus thermophillus* ferment extract) is optionally included. In one embodiment, effective amounts include, but are not limited to, the following amounts: the first anti-melanin agent is provided in a range of 0.05-5%, the second anti-melanin agent is provided in a range of 0.005-5%, the anti-inflammatory agent is provided in a range of 0.05-5%, the zinc oxide is provided in a range of 5-15% and the titanium dioxide in a range of 10-15%, wherein the ranges are provided as % m/m, % m/v, or % v/v of the formulation.

In several embodiments, topical formulations for treating skin redness and/or irritation, and methods of using same, are provided. In some embodiments, the formulation comprises niacinamide, a *Zingiber officinale* root extract, bisabolol, a *Chrithmum maritimum* extract, a *Magnolia officinalis* bark extract, a Vitamin E compound; a zinc oxide and a titanium dioxide. The formulation, in one embodiment, provides a sun protection factor of SPF 15, 30, 50 or more and is in the form of a liquid (e.g., liquid lotion, liquid serum), cream or gel (e.g., ointment gel). Caprylic/capric triglycerides, siloxane and/or beta-glucan may be included in one embodiment. Effective amounts of the active ingredients are provided in many embodiments, including but not limited to, *Zingiber officinale* root extract in a range of 0.005-5%, bisabolol in a range of 0.05-5%, *Chrithmum maritimum* extract in a range of 0.02-5%, *Magnolia officinalis* bark extract in a range of 0.001-5%, Vitamin E compound in a range of 0.05-5%, niacinamide in a range of 0.05-5%, zinc oxide in a range of 5-15%; and titanium dioxide in a range of 10-15%, wherein the ranges are provided as % m/m, % w/w, % w/v, % m/v, or % v/v of the formulation.

In some embodiments, topical formulations for treating skin redness and/or irritation, and methods of using same, are provided that comprise: (i) a first skin conditioning agent, (ii) a second skin conditioning agent, (iii) a third skin conditioning agent, (iv) a fourth agent, (v) an anti-inflammatory agent, and optionally (vi) a sun protection agent. In several embodiments, the first skin conditioning agent comprises *Zingiber* (e.g., a *Zingiber officinale* extract), the second skin conditioning agent comprises an asteraceae extract and/or bisabolol, the third skin conditioning agent comprises *Crithmum* (e.g., a *Crithmum maritimum* extract), the fourth agent comprises an antimicrobial and can optionally also serves as a skin conditioning agent, and the anti-inflammatory agent comprises a Vitamin E compound (e.g., disodium lauriminodipropionate tocopheryl phosphates). In one embodiment, the sun protection agent comprises zinc oxide and/or titanium dioxide at an SPF of 15, 30 or 50 (or more). In one embodiment, one, two or all of the following are also included: caprylic/capric triglycerides, niacinamide, a beta-glucan compound, siloxane (e.g., cyclopentasiloxane). Root extracts are provided in some embodiments. In one embodiment, the first skin conditioning agent is provided in a range of 0.005-5%, the second skin conditioning agent is provided in a range of 0.05-5%, the third skin conditioning agent is provided in a range of 0.02-5%, the fourth agent is provided in a range of 0.001-5%, and the anti-inflammatory agent is provided in a range of 0.05-5%. In one embodiment, the zinc oxide is provided in a range of 5-15% and the titanium dioxide in a range of 10-15%. The ranges may be provided as % m/m, % w/w, % w/v, % m/v, or % v/v of the formulation.

In some embodiments, topical formulations for mediating an inflammatory pathway, and methods of using same, are provided that comprise: Niacinamide, bisabolol, tocopheryl phosphate, a *Crithmum* extract, optionally a *Crithmum maritimum* extract, a *Magnolia* extract, optionally *Magnolia officinalis* extract, and a *Zingiber* extract, optionally a *Zingiber officinale* extract. Beta-glucan and/or jojoba compounds may also be included in one embodiment. The formulations may be particularly beneficial in some embodiments because they exhibit one or more of the following effects: (i) inflammation is reduced; (ii) cytokines are reduced; (iii) skin irritation is reduced; and (iv) skin redness is reduced. In one embodiment, these effects are reduced by 10-50% post treatment with the formulation 1-3 times daily after 7, 14, 21, 30, 60 or 90 days, as compared to no treatment or treatment without the ingredients described herein. In one embodiment, skin redness is reduced within 24 hours of use of the formulation and inflammation is reduced for at least several hours or days thereafter, thereby providing both instant and long-lasting effects.

In some embodiments, topical formulations for treating skin, and methods of using same, are provided that comprise a vitamin E compound, a ginger root extract; and bisabolol. In other embodiments, a formulation is provided that comprises an antioxidant to soothe redness and inflammation related to environmental and mechanical factors, a first plant extract to restore water balance, a second extract and third plant extract, or synthetic version thereof, to reduce redness, inflammation, heat and/or discomfort, a fourth plant extract to reduce skin redness and/or enhancing the appearance of skin firmness and/or hydration, a compound to reduce sensitive, red and itching skin while helping to reduce dryness and enhance the skin barrier, a vitamin compound to skin, aide the skin barrier, reduce the appearance of redness/blotchiness, help balance sebum production and improve the appearance of skin imperfections, an optional colorant having a greenish tint or other tint to counteract the appearance of redness, and an optional SPF of at least 15, 30 or 50. In one embodiment, a formulation is provided that comprises a bio-available form of vitamin E that functions as an antioxidant to soothe redness and inflammation related to environmental and mechanical factors, a marine plant extract from sea fennel to restore water balance, a ginger extract and bisabolol to reduce redness, inflammation, heat and/or discomfort, a *magnolia* bark extract to reduce skin redness and enhancing the appearance of skin firmness and/or hydration, a derivative of baker's yeast ß-glucan to reduce sensitive, red and/or itching skin while helping to reduce dryness and/or enhance the skin barrier, niacinamide to soothe skin, aide the skin barrier, reduce the appearance of redness/blotchiness, help balance sebum production and/or improve the appearance of skin imperfections, am optional colorant having a greenish tint or other tint to counteract the appearance of redness, and an SPF of at least 15, 30 or 50.

In several embodiments, the formulations to reduce skin redness and/or irritation is a liquid, cream or gel, which includes for examples serums and ointments. The formulations may be free of parabens and/or animal products. In one embodiment, the formulations decrease inflammatory mediators. The formulations may increase skin hydration and/or improve barrier functions of the epidermal layer. In several embodiments, the sunscreens provided are mineral sunscreens that are chemical free. In many embodiments, the formulation neutralizes redness, acts as a moisturizing color corrector and sunscreen all in one.

DETAILED DESCRIPTION

Eye Renewal and Skin Formulations

As described above, several embodiments of the present invention relate to unique topical cosmetic skin care formulations for treating, protecting, and/or repairing skin, such as skin around the delicate eye area. The formulations described herein can be beneficial for both healthy and damaged skin, for example skin that is irritated through aging, sun exposure, or other environmental stress. In several embodiments, use of the formulations described herein provides one or more of the following advantages: (i) brightens and corrects dark circles, (ii) reduces puffiness, (iii) smooths fine lines and wrinkles, (iii) protects against sun damage, (iv) hydrates, and (v) primes skin for smooth application of eye makeup. Additionally, several embodiments described herein provide a rejuvenated, refreshed and more youthful appearance after daily use for 2, 4 or 6 weeks. Advantageously, in several embodiments, these improvements are obtained in a single formulation (rather than multiple formulations that are applied separately) that is gentle and non-irritating, with no or little stinging, tingling, or burning sensation. Because undesired effects are nominal or nonexistent, the formulation fosters regular use by a subject (even one with sensitive skin), which enables longer term improvements in skin characteristics.

In several embodiments, the formulations described herein are free from one or more (or all) of the following: parabens, sulfates, phthalates, synthetic fragrance, talc, dyes, mineral oils, drying alcohols, glycol, gluten, and chemical sunscreen. In several embodiments, the formulations are safe for contact lens wearers. In several embodiments, the formulations are hypoallergenic and noncomedogenic. In several embodiments, the formulation is vegan and free from animal products (e.g., the components of the formulation are plant-based or synthetic). In several embodiments, the formulations provided for herein are suitable for 1, 2, or 3× daily topical application, and rated at Protection Grade of Ultraviolet A (PA) of 12 or greater in a Persistent Pigment Darkening (PPD) test. In several embodiments, the formulations provided for herein are rated at Protection Grade of Ultraviolet A (PA) of 14 or greater, 16 or greater, or 18 or greater (or any rating therebetween) in a Persistent Pigment Darkening (PPD) test. In one embodiment, the formulation is left on overnight to provide benefits.

The formulations described herein can provide both short-term and long-term benefits according to several embodiments. Beneficial effects from use of the formulations described herein occur upon use, within 1-2 days, about 7 days, about 14 days, or within about 4 weeks. In several embodiments, the skin appears improved after application of the formulation and benefits continue over about 2-6 weeks, about 6-12 weeks, about 12-24 weeks, or about 24-52 weeks of use. In several embodiments, long lasting effects on the skin are achieved in less than 1-3 months.

Several embodiments of the invention comprise a formulation for soothing irritated skin while also reinforcing the skin's natural defenses. In some embodiments, the formulation optionally includes ingredients that provide protection against UV damage. In some embodiments, the formulation is a liquid, gel, cream or serum. Solid forms (e.g., powders) may be provided. The formulations described herein can be applied prior to or after foundation or other make-up. In some embodiments, the formulation is colorless (e.g., clear); however, in other embodiments, the formulation contains sufficient color to serve as foundation and/or color corrector (e.g., with peach undertones to balance dark areas). In some embodiments, the pH of the formulations is slightly basic, slightly acidic or neutral. In some embodiments, a pH of 3-5, 4-6, 5-7, 6-8, or ranges in between, are provided. Lower or higher pH values may also be used. In one embodiment, a clear formulation is provided in which, for example, titanium dioxide, zinc oxide and colorants are not included. In some embodiments, a clear formulation without titanium dioxide, zinc oxide or colorants is provided as a serum in which the ingredients are concentrated by at least 10-50% or 2-15×, as compared to the formulations containing titanium dioxide, zinc oxide and colorants.

According to several embodiments, the formulations described herein can be applied by an applicator, including one with a smooth metallic tip, a roller ball tip, a plastic tip, or combinations thereof. In one embodiment, the tip has a different thermal conductivity than the body of the applicator to cause a cooling effect at the tip that helps reduces puffiness. The size of the applicator tips may be configured for the region to be treated. For example, the eye area, nasolabial folds and marionette lines may be suited for a smaller tip than larger target regions. Alternatively, the formulations may be applied by hand, by sponge, by spraying, by dropper, by brush, or through use of a composition-impregnated substrate (such as silicone pads or wipes).

In some embodiments, the formulations described herein can optionally be applied by transdermal patch. In some embodiments, the formulations are absorbent (e.g., readily absorbable) such that no separate means are needed to enhance absorption. However, in alternate embodiments, one or more of massage, mechanical manipulation, energy, or vibration may be used to facilitate absorption. In some embodiments, the formulation is useful post-surgery or dermatological treatment. Further, some of the formulations described herein may be suitable for use for application under one or more skin layers (e.g., as an injectable)

In some embodiments, the formulation comprises, consists essentially of or consists of several (e.g., 6, 8, 10) or all of the following groups of ingredients listed in Table 1 below.

TABLE 1

| Group | Example ingredients in each group | % in total formula in some embodiments as, for example, % m/m, % m/v, % w/w, % w/v or % v/v |
|---|---|---|
| Group 1A | One or more solvents such as water, siloxanes (e.g., cyclopentasiloxane), caprylic/capric triglycerides and/or glycerin | about 20-60% (e.g., about 25, 35, 45, 55%) |
| Group 1B | A silicone elastomer blend to, for example, act as an emollient, skin conditioning agent, dispersing agent and/or viscosity increasing agent. These include, for example, siloxanes (e.g., cyclopentasiloxane), dimethicone crosspolymer, dimethicone/vinyl dimethicone crosspolymer, and/or dimethiconol | about 2-20% (e.g., about 5, 6, 7, 8, 9, 10, 11, 12, 15%) |
| Group 1C | One or more ultraviolet (UV) absorbing agents, such as zinc oxide and/or titanium dioxide | about 2-20% (e.g., about 5, 6, 7, 8, 9, 10, 11, 12, 15%) |
| Group 1D | One or more skin conditioning and/or emollient agents such as caprylic/capric triglyceride, jojoba esters, glyceryl behenate/eicosadioate, lauryl polyglyceryl-3 polydimethylsiloxyethyl dimethicone, tocopherol, lauroyl lysine, palmitoyl tripeptide-5, glycerin, panthenol, pantolactone, and/or ethylhexylglycerin, | about 5-30% (e.g., about 7, 9, 11, 13, 15, 18, 20, 22, 25, 28%) |
| Group 1E | One or more agents for anticaking, bulking and/or opacifying such as silica, mica and/or alumina | about 0.1-4% (e.g., about 0.5, 0.8, 1, 1.2, 1.5, 2, 2.5, 3%) |
| Group 1F | One or more colorant agents such as iron oxides (e.g., Cl 77491, Cl 77499, and/or Cl 77492) | about 0.1-4% (e.g., about 0.5, 0.8, 1, 1.2, 1.5, 2, 2.5, 3%) |
| Group 1G | One or more agents for dermal strengthening and anti-glycation, hydration and anti-oxidant activity such as Albizia (e.g., Albizia julibrissin extract), Centella (e.g., Centella asiatica, an asiaticoside extracted therefrom), Siegesbeckia (e.g., Siegesbeckia orientalis, a darutoside extracted therefrom), sodium hyaluronate, Dunaliella (e.g., Dunaliella sauna extract), sea water, algin (such as hydrolyzed algin), Tremella (e.g., Tremella fuciformis sporocarp extract), betaine, glycerin, Ascophyllum (e.g., Ascophyllum | about 0.5-10% (e.g., about 0.8, 1, 1.5, 2, 3, 4, 5, 6, 8%) |

TABLE 1-continued

| Group | Example ingredients in each group | % in total formula in some embodiments as, for example, % m/m, % m/v, % w/w, % w/v or % v/v |
|---|---|---|
| | nodosum extract), and/or Asparagopsis (e.g., Asparagopsis armata extract) | |
| Group 1H | One or more agents that act as a preservative and/or biocide such as phenoxyethanol, sodium benzoate, citric acid, and/or potassium sorbate | about 0.1-4% (e.g., about 0.5, 0.8, 1, 1.2, 1.5, 2, 2.5, 3%) |
| Group 1I | One or more dispersing agents such as polyhydroxystearic acid | about 0.01-2% (e.g., about 0.05, 0.1, 0.2, 0.5, 1, 1.5%) |
| Group 1J | One or more agents for adjusting pH and/or chelation such as citric acid | about 0.01-2% (e.g., about 0.05, 0.1, 0.2, 0.5, 1, 1.5%) |
| Group 1K | One or more agents that act as a humectant such as sucrose, sea water sorbital, betaine, Tremella (e.g., tremella fuciformis sporocarp), glycerin, pantolactone, and/or panthenol | about 2-20% (e.g., about 5, 6, 7, 8, 9, 10, 11, 12, 15%) |
| Group 1L | One or more viscosity balancing (increasing or decreasing) agents such as sodium chloride, dimethicone (e.g., lauryl polyglyceryl-3 polydimethylsiloxyethyl dimethicone), algin (e.g., hydrolyzed algin), hydrogenated polyisobutene and/or glycerin | about 2-25% (e.g., about 5, 6, 7, 8, 9, 10, 11, 12, 15, 20%) |
| Group 1M | One or more agents that act as a binder such as triethoxycaprylylsilane | about 0.001-2% (e.g., about 0.005, 0.01, 0.02, 0.03, 0.05, 0.1, 0.2, 0.5, 1, 1.5%) |
| Group 1N | One or more surfactant and/or solubilizing agents such as dimethicone (e.g., lauryl polyglyceryl-3 polydimethylsiloxyethyl dimethicone), and/or glyceryl behenate/eicosadioate | about 0.1-10% (e.g., about 0.2, 0.5, 1, 3, 5, 7%) |

In some embodiments, the formulation comprises, consists essentially of or consists of several (e.g., 8, 10, 12) or all of the following groups of ingredients listed in Table 2 below:

TABLE 2

| Group | Example ingredients in each group | % in total formula in some embodiments as, for example, % m/m, % m/v, % w/w, % w/v or % v/v |
|---|---|---|
| Group 2.1 | Water | about 20-60% (e.g., about 25, 35, 45, 55%) |
| Group 2.2 | Hydrogenated polyisobutene | about 2-20% (e.g., about 4, 5, 6, 7, 8, 9, 10, 12, 15%) |
| Group 2.3 | At least two (or all of): siloxanes (e.g., cyclopentasiloxane), dimethicone crosspolymer, dimethicone/ vinyl dimethicone crosspolymer, and dimethiconol | about 2-20% (e.g., about 4, 5, 6, 7, 8, 9, 10, 12, 15%) as a group, wherein individual ingredients are about 0.04-15% (e.g., about 0.05, 0.15, 0.2, 0.25, 0.8, 1, 3, 4, 6, 7, 8, 12, 14%) |
| Group 2.4 | At least two (or all of): zinc oxide (e.g., Cl 77947), caprylic/capric triglyceride, jojoba esters, and glyceryl behenate/eicosadioate | about 2-20% (e.g., about 4, 5, 6, 7, 8, 9, 10, 12, 15%) as a group, wherein individual ingredients are about 0.04-15% (e.g., about 0.05, 0.15, 0.2, 0.25, 0.8, 1, 3, 4, 6, 7, 8, 12, 14%) |
| Group 2.5 | At least two (or all of): titanium dioxide (e.g., Cl 77891), triglyceride | about 1-15% (e.g., about 2, 3, 4, 5, 6, 7, 8, 9, 10, 12, 15%) as a group, |

TABLE 2-continued

| Group | Example ingredients in each group | % in total formula in some embodiments as, for example, % m/m, % m/v, % w/w, % w/v or % v/v |
|---|---|---|
| | (e.g., caprylic/capric triglyceride), silica, polyhydroxystearic acid, and alumina | wherein individual ingredients are about 0.04-12% (e.g., about 0.05, 0.1, 0.15, 0.2, 0.25, 0.8, 1, 3, 3.5 4, 6, 7, 8, 10%) |
| Group 2.6 | One or both of dimethicone (e.g., lauryl polyglyceryl-3 polydimethylsiloxyethyl dimethicone) and tocopherol | about 1-15% (e.g., about 2, 3, 4, 5, 6, 7, 8, 9, 10, 12, 15%) as a group, wherein individual ingredients are about 0.0005-10% (e.g., about 0.001, 0.005, 0.01, 0.06, 0.2, 0.5, 1, 3, 4, 5, 6, 7, 8%) |
| Group 2.7 | One or both of titanium dioxide (e.g., Cl 77891) and dimethicone | about 1-15% (e.g., about 2, 3, 4, 5, 6, 7, 8, 9, 10, 12, 15%) as a group, wherein individual ingredients are about 0.0005-10% (e.g., about 0.001, 0.005, 0.01, 0.06, 0.2, 0.5, 1, 3, 4, 5, 6, 7, 8%) |
| Group 2.8 | One or both of mica and lauroyl lysine | about 0.1-7% (e.g., about 0.5, 1, 2, 3, 4, 5, 6%) as a group, wherein individual ingredients are about 0.0005-5% (e.g., about 0.001, 0.005, 0.01, 0.03 0.06, 0.2, 0.5, 1, 3, 4%) |
| Group 2.9 | At least two (or all of): glycerin, Albizia (e.g., Albizia julibrissin bark extract), sodium benzoate, Centella (e.g., Centella asiatica, an asiaticoside extracted therefrom), Siegesbeckia (e.g., Siegesbeckia orientalis, a darutoside extracted therefrom) | about 0.1-7% (e.g., about 0.5, 1, 2, 3, 4, 5, 6%) as a group, wherein individual ingredients are about 0.0005-5% (e.g., about 0.001, 0.002, 0.004, 0.005, 0.01, 0.03 0.06, 0.2, 0.5, 0.8, 1, 2, 3, 4%) |
| Group 2.10 | At least two (or all of): palmitoyl tripeptide-5, panthenol, sodium hyaluronate, Dunaliella (e.g., Dunaliella salina extract), phenoxyethanol, citric acid, sodium benzoate ethylhexylglycerin, potassium sorbate, pantolactone, and water | about 0.1-6% (e.g., about 0.5, 1, 1.5, 2, 3, 4, 5%) as a group, wherein individual ingredients are about 0.001-4% (e.g., about 0.002, 0.003, 0.004, 0.005, 0.01, 0.02, 0.03, 0.06, 0.09, 0.1, 0.2, 0.5, 0.8, 1, 1.5, 2, 3, 4%) |
| Group 2.11 | At least two (or all of): water (such as sea water), algin (such as hydrolyzed algin), sucrose, phenoxyethanol, and ethylhexylglycerin | about 0.1-4% (e.g., about 0.5, 1, 1.5, 2, 3%) as a group, wherein individual ingredients are about 0.0005-4% (e.g., about 0.001, 0.002, 0.005, 0.01, 0.02, 0.03, 0.06, 0.09, 0.1, 0.2, 0.5, 0.7, 0.8, 1, 1.5, 2, 3%) |
| Group 2.12 | At least two (or all of): sorbital, water, Ascophyllum (e.g., Ascophyllum nodosum extract), Asparagopsis (e.g., Asparagopsis armata extract), phenoxyethanol, and potassium sorbate | about 0.1-4% (e.g., about 0.5, 0.9, 1, 1.1, 1.5, 2, 3%) as a group, wherein individual ingredients are about 0.0005-3% (e.g., about 0.001, 0.002, 0.005, 0.007, 0.01, 0.02, 0.03, 0.06, 0.09, 0.1, 0.2, 0.4, 0.5, 0.7, 0.8, 1, 1.5, 2%) |
| Group 2.13 | At least two (or all of): water, tremella (e.g., Tremella fuciformis sporocarp extract), betaine, glycerin, potassium sorbate, and phenoxyethanol | about 0.1-4% (e.g., about 0.5, 0.9, 1, 1.1, 1.5, 2, 3%) as a group, wherein individual ingredients are about 0.0005-3% (e.g., about 0.002, 0.003, 0.004, 0.007, 0.01, 0.02, 0.03, 0.06, 0.08, 0.09, 0.1, 0.2, 0.5, 0.7, 0.8, 1, 1.5, 2%) |
| Group 2.14 | Sodium chloride | 0.01-5% (e.g., about 0.05, 0.1, 0.15, 0.2, 0.5, 0.7, 0.8, 1, 2, 4%) |
| Group 2.15 | At least two (or all of): phenoxyethanol, ethylhexylglycerin and tocopherol | about 0.01-4% (e.g., about 0.2, 0.4, 0.5, 0.9, 1, 1.5, 2, 3%) as a group, wherein individual ingredients are about 0.0001-3% (e.g., about 0.0005, 0.001, 0.007, 0.02, 0.08, 0.1, 0.2, 0.4, 0.7, 0.8, 0.9, 1, 1.5, 2%) |
| Group 2.16 | At least one (or all of): iron oxides (e.g., Cl 77491, Cl 77499, and/or Cl 77492) and triethoxycaprylylsilane | about 0.01-4% (e.g., about 0.2, 0.4, 0.5, 0.9, 1, 1.1, 1.2, 1.5, 2, 3%) as a group, wherein individual ingredients are about 0.0001-3% (e.g., about 0.002, 0.009, 0.01, 0.02, 0.08, 0.1, 0.2, 0.4, 0.7, 0.8, 0.9, 1, 1.5, 2%) |

In some embodiments, the formulation comprises, consists essentially of or consists of several (e.g., 6, 8, 10) or all of the following groups of ingredients listed in Table 3 below.

TABLE 3

| Group | Example ingredients in each group | % in total formula in some embodiments as, for example, % m/m, % m/v, % w/w, % w/v or % v/v |
|---|---|---|
| 3.1 | water | about 60-95% (e.g., about 65, 70, 80, 85, 90%) |
| 3.2 | water, sorbitol, Ascophyllum nodosum extract, Asparagopsis armata extract | about 0.2-5% (e.g., about 0.5, 0.8, 1, 1.5, 2, 4%) |
| 3.3 | palmitoyl tripeptide-5, panthenol, sodium hyaluronate, Dunaliella salina extract | about 0.5-6% (e.g., about 0.8, 1, 1.5, 2, 3, 4, 5%) |
| 3.4 | sea water, water, hydrolyzed algin, sucrose | about 0.2-5% (e.g., about 0.5, 0.8, 1, 1.5, 2, 4%) |
| 3.5 | glycerin, Albizia julibrissin bark extract, darutoside | about 0.5-6% (e.g., about 0.8, 1, 1.5, 2, 3, 4, 5%) |
| 3.6 | water, Tremella fuciformis sporocarp (silver ear mushroom) extract, betaine, glycerin | about 0.2-5% (e.g., about 0.5, 0.8, 1, 1.5, 2, 4%) |
| 3.7 | glycerin | about 0.2-5% (e.g., about 0.5, 0.8, 1, 1.5, 2, 4%) |
| 3.8 | xanthan gum | about 0.05-3% (e.g., about 0.1, 0.35, 0.4, 0.5, 0.85, 1, 2%) |
| 3.9 | polysorbate 20 | about 0.05-3% (e.g., about 0.1, 0.35, 0.4, 0.5, 0.85, 1, 2%) |
| 3.10 | phenoxyethanol, ethylhexylglycerin | about 0.05-3% (e.g., about 0.1, 0.35, 0.4, 0.5, 0.85, 1, 2%) |
| 3.11 | caprylyl glycol, caprylhydroxamic acid, glycerin | about 0.05-3% (e.g., about 0.1, 0.35, 0.4, 0.5, 0.85, 1, 2%) |

In some embodiments, formulations according to each of Tables 1-3 have a pH at 25 degrees Celsius of about 5.5-7.7 (e.g., 6-7).

In the tables above, the ranges provided in the parentheticals include the overlapping ranges between the numbers. For example, a range of 20-60% (e.g., about 25, 35, 45, 55%) includes, for example, ranges between 25-35%, 25-55%, 45-55%, 35-55%, etc.). In one embodiment, the percentages provided are % m/m or % w/w.

In one embodiment, the formulation comprises or consists essentially of water, *Albizia* (such as *Albizia Julibrissin*), *Tremella* (such as *Tremella fuciformis* sporocarp), algin (such as hydrolyzed algin), *Ascophyllum* (such as *Ascophyllum nodosu*), betaine, *Dunaliella* (such as *Dunaliella salina*), *Asparagopsis* (such as *Asparagopsis armata*), *Centella* (e.g., *Centella asiatica* or an *asiaticoside* extracted therefrom), *Siegesbeckia* (e.g., *Siegesbeckia orientalis* or a darutoside extracted therefrom), and one or more ingredients selected from the group consisting of titanium dioxide, zinc oxide, polyisobutenes, siloxanes, triglycerides, sorbitol, jojoba, glycerin, panthenol, mica, dimethicones, lauroyl lysine, ethylhexylglycerin, triethoxycaprylylsilane, alumina, phenoxyethanol, potassium sorbate, sodium benzoate, citric acid and iron oxides.

In one embodiment, the formulation comprises or consists essentially of (i) water in a range of about 30-90% of the total formulation, (ii) titanium dioxide and zinc oxide collectively in a range of about 5-20% of the total formulation, (iii) at least five or all of *Albizia* (such as *Albizia julibrissin*), *Tremella* (such as *Tremella fuciformis* sporocarp), algin (such as hydrolyzed algin), *Ascophyllum* (such as *Ascophyllum nodosu*), betaine, *Dunaliella* (such as *Dunaliella salina*), *Asparagopsis* (such as *Asparagopsis armata*), *Centella* (e.g., *Centella asiatica* or an *asiaticoside* extracted therefrom), *Siegesbeckia* (e.g., *Siegesbeckia orientalis* or a darutoside extracted therefrom), collectively in a range of about 0.3-10% of the total formulation, and (iv) at least five or all of polyisobutenes, siloxanes, triglycerides, sorbitol, jojoba, glycerin, panthenol, mica, dimethicones, lauroyl lysine, ethylhexylglycerin, triethoxycaprylylsilane, alumina, phenoxyethanol, potassium sorbate, sodium benzoate, citric acid and iron oxides, collectively in a range of about 5-50% of the total formulation. In one embodiment, the percentages provided are % m/m or % w/w.

In one embodiment, the formulation comprises or consists essentially of (i) water in a range of about 30-90% of the total formulation, (ii) titanium dioxide and zinc oxide collectively in a range of about 5-20% of the total formulation, (iii) at least five or all of *Albizia* (such as *Albizia julibrissin*), *Tremella* (such as *Tremella fuciformis* sporocarp), algin (such as hydrolyzed algin), *Ascophyllum* (such as *Ascophyllum nodosu*), betaine, *Dunaliella* (such as *Dunaliella salina*), *Asparagopsis* (such as *Asparagopsis armata*), *Centella* (e.g., *Centella asiatica* or an *asiaticoside* extracted therefrom), *Siegesbeckia* (e.g., *Siegesbeckia orientalis* or a darutoside extracted therefrom), collectively in a range of about 0.3-10% of the total formulation, and (iv) preservatives, viscosity increasing/decreasing agents, surfactants, emulsifiers, fragrances, colorants, and solvents, collectively in a range of about 5-50% of the total formulation. In one embodiment, the percentages provided are % m/m or % w/w.

In several embodiments, the formulation comprises or consists essentially of an *Albizia* extract, a *Tremella* extract, a brown seaweed extract, an *Ascophyllum* extract, a *Dunaliella* extract, an *Asparagopsis* extract, a *Centella* extract and a *Siegesbeckia* extract.

In several embodiments, the formulation comprises or consists essentially of an *Albizia* extract, a *Tremella* extract, a brown seaweed extract, an *Ascophyllum* extract, a *Dunaliella* extract, an *Asparagopsis* extract, and a darutoside In some embodiments, the formulation comprises or consists essentially of marine microalgae, at least two polysaccharides, a plant-based water-retention agent, and at least two plant extracts. In one embodiment, the marine microalgae are in a range of about 0.01-5%, the polysaccharides are in a range of about 0.01-5%, the plant-based water-retention agent is provided in a range of about 0.01-5%, and the plant extracts are provided in a range of about 0.01-5%. In one embodiment, the percentages provided are % m/m or % w/w.

In several embodiments, the formulation comprises or consists essentially of (i) one or more solvents in a range of about 30-95% of the total formulation, and (ii) *Albizia, Tremella*, algin, *Ascophyllum, Dunaliella, Asparagopsis, Centella*, and *Siegesbeckia*, or extracts thereof, and betaine, collectively in a range of about 0.3-10% of the total formulation. In some embodiments, these ingredients are provided in a clear serum without, for example, titanium dioxide, zinc oxide or colorants, and such ingredients are concentrated by at least 10-50% or 2-15×, as compared the amounts listed on Table 3. In one embodiment, the following ingredients are also provided: a preservative, a viscosity increasing/decreasing agent, a surfactant, an emulsifier, a fragrance, and a colorant, collectively in a range of about 5-50% of the total formulation. Optionally, titanium dioxide and zinc oxide are provided collectively in a range of about 5-20% of the total formulation. In one embodiment, the percentages provided are % m/m or % w/w.

In one embodiment, the formulation comprises or consists essentially of (i) water in a range of about 30-95% of the total formulation, (ii) at least five or all of *Albizia* (such as *Albizia julibrissin*), *Tremella* (such as *Tremella fuciformis* sporocarp), algin (such as hydrolyzed algin), *Ascophyllum* (such as *Ascophyllum nodosu*), betaine, *Dunaliella* (such as *Dunaliella salina*), *Asparagopsis* (such as *Asparagopsis armata*), *Centella* (e.g., *Centella asiatica* or an *asiaticoside* extracted therefrom), *Siegesbeckia* (e.g., *Siegesbeckia orientalis* or a darutoside extracted therefrom), collectively in a range of about 0.3-10% of the total formulation, and (iii) at least five or all of titanium dioxide, zinc oxide polyisobutenes, siloxanes, triglycerides, sorbitol, jojoba, glycerin, panthenol, mica, dimethicones, lauroyl lysine, ethylhexylglycerin, triethoxycaprylylsilane, alumina, phenoxyethanol, potassium sorbate, sodium benzoate, citric acid and iron oxides, collectively in a range of about 5-50% of the total formulation. In one embodiment, the percentages provided are % m/m or % w/w.

In some embodiments, the formulation comprises or consists essentially of (i) water in a range of about 30-95% of the total formulation, (ii) at least five or all of *Albizia* (such as *Albizia julibrissin*), *Tremella* (such as *Tremella fuciformis* sporocarp), algin (such as hydrolyzed algin), *Ascophyllum* (such as *Ascophyllum nodosu*), betaine, *Dunaliella* (such as *Dunaliella salina*), *Asparagopsis* (such as *Asparagopsis armata*), *Centella* (e.g., *Centella asiatica* or an *asiaticoside* extracted therefrom), *Siegesbeckia* (e.g., *Siegesbeckia orientalis* or a darutoside extracted therefrom), collectively in a range of about 0.3-10% of the total formulation, and (iii) preservatives, viscosity increasing/decreasing agents, surfactants, emulsifiers, and solvents, collectively in a range of about 5-50% of the total formulation. In one embodiment, also included are colorants, fragrances, titanium dioxide and zinc oxide collectively in a range of about 5-20% of the total formulation. In one embodiment, the percentages provided are % m/m or % w/w.

In several embodiments, the formulation comprises or consists essentially of (i) water and glycerin in a range of about 60-98%, (ii) *Ascophyllum* (such as *Ascophyllum nodosu*) and/or *Asparagopsis* (such as *Asparagopsis armata*) in a range of about 0.1-2%, (iii) one or more of palmitoyl tripeptide-5, panthenol, sodium hyaluronate, and *Dunaliella* (such as *Dunaliella salina*) in a range of about 0.5-8%, (iv) algin (such as hydrolyzed algin) in a range of about 0.01-5%, (v) *Albizia* (such as *Albizia julibrissin*) and/or darutoside (e.g., a darutoside extracted *Siegesbeckia orientalis*) in a range of about 0.5-6%, (vi) *Tremella* (such as *Tremella fuciformis* sporocarp), (vii) two or more of sucrose, betaine, xanthan gum, polysorbate 20, phenoxyethanol, ethylhexylglycerin, caprylyl glycol, caprylhydroxamic acid, sorbitol in a range of about 0.5-15%. In one embodiment, the percentages of ingredients are provided are % m/m or % w/w as compared to the total formulation.

In several embodiments, the formulation comprises or consists essentially of effective amounts of (i) *Ascophyllum* (such as *Ascophyllum nodosu*) and/or *Asparagopsis* (such as *Asparagopsis armata*) (ii) one or more of palmitoyl tripeptide-5, panthenol, sodium hyaluronate, and *Dunaliella* (such as *Dunaliella salina*), (iii) algin (such as hydrolyzed algin), (v) *Albizia* (such as *Albizia julibrissin*) and/or darutoside (e.g., a darutoside extracted from *Siegesbeckia orientalis*), and (vi) *Tremella* (such as *Tremella fuciformis* sporocarp). In one embodiment, two or more of the following are also included: water, glycerin, sucrose, betaine, xanthan gum, polysorbate 20, phenoxyethanol, ethylhexylglycerin, caprylyl glycol, caprylhydroxamic acid, and sorbitol.

In some embodiments, the formulation comprises or consists essentially of effective amounts of four or more of the following: *Ascophyllum* (such as *Ascophyllum nodosu*), *Asparagopsis* (such as *Asparagopsis armata*), palmitoyl tripeptide-5, panthenol, sodium hyaluronate, *Dunaliella* (such as *Dunaliella salina*), algin (such as hydrolyzed algin), *Albizia* (such as *Albizia julibrissin*), darutoside (e.g., a darutoside extracted from *Siegesbeckia orientalis*), and *Tremella* (such as *Tremella fuciformis* sporocarp). In one embodiment, two or more of the following are also included: water, glycerin, sucrose, betaine, xanthan gum, polysorbate 20, phenoxyethanol, ethylhexylglycerin, caprylyl glycol, caprylhydroxamic acid, and sorbitol.

In some embodiments, a topical skin care formulation, comprising effective amounts of the following ingredients is provided: an *Albizia julibrissin* extract, a *Dunaliella salina* extract, a hydrolyzed algin, a betaine, an *Ascophyllum nodosum* extract, an *Asparagopsis armata* extract, a *Tremella fuciformis* sporocarp extract, and a darutoside. These ingredients are provided in a range of 0.3-15% (e.g., 0.3-10%) of the formulation and may further comprise one or more solvents (such as water) provided in a range of 50-95% of the formulation.

In some embodiments, a topical skin care formulation, comprising the following is provided: a combination of *Albizia, Tremella*, algin, *Ascophyllum*, betaine, *Dunaliella, Asparagopsis*, and one or both of a darutoside and an *asiaticoside*, collectively in a range of about 0.3-10% of the total formulation; a combination of palmitoyl tripeptide-5, panthenol, sodium hyaluronate, sucrose, glycerin, phenoxyethanol, and ethylhexylglycerin, caprylyl glycol, and caprylhydroxamic acid, collectively in a range of about 2-50% of the total formulation; and water in a range of about 30-95% of the total formulation. A topical skin care formulation comprising the following provided in several embodiments: a combination of *Albizia, Tremella*, algin, *Ascophyllum*, betaine, *Dunaliella, Asparagopsis*, and a darutoside, said combination in a range of about 0.3-10% of the total formulation; one or more preservatives, viscosity agents, and emulsifiers, collectively in a range of about 2-20% of the total formulation; and one or more solvents in a range of about 30-95% of the total formulation. In some embodiments, the *Albizia* comprises *Albizia Julibrissin* or an extract thereof, the *Tremella* comprises *Tremella fuciformis* sporocarp or an extract thereof, the algin comprises hydrolyzed algin, the *Ascophyllum* comprises *Ascophyllum nodosu* or an extract thereof, the *Dunaliella* comprises *Dunaliella salina* or an extract thereof, and the *Asparagopsis* comprises *Asparagopsis armata* or an extract thereof.

In one embodiment, the formulation comprises aqua/water, hydrogenated polyisobutene, titanium dioxide, zinc oxide, cyclopentasiloxane, caprylic/capric triglyceride, lauryl polyglyceryl-3 polydimethylsiloxyethyl dimethicone, glycerin, panthenol, mica, dimethicone crosspolymer, *Albizia julibrissin* extract, sea water, sorbitol, jojoba esters, sodium hyaluronate, palmitoyl tripeptide-5, *Tremella fuciformis* sporocarp extract, hydrolyzed algin, *Ascophyllum nodosum* extract, betaine, *dunaliella salina* extract, *Asparagopsis armata* extract, sucrose, darutoside, pantolactone, tocopherol, sodium chloride, dimethicone/vinyl dimethicone crosspolymer, silica, polyhydroxystearic acid, glyceryl behenate/eicosadioate, dimethicone, lauroyl lysine, dimethiconol, ethylhexylglycerin, triethoxycaprylylsilane, alumina, phenoxyethanol, potassium sorbate, sodium benzoate, citric acid and iron oxides (e.g., CI 77491, CI 77492, CI 77499, and/or CI 77891). In one embodiment, glyceryl behenate/eicosadioate is a combination of esters of glycerin with behenic andeicosanoic acids.

In several embodiments in which darutoside is included in the formulation, the darutoside is obtained from *Siegesbeckia* (such as *Siegesbeckia orientalis*). In one embodiment, darutoside is used for strengthening of dermal tissue. In one embodiment, darutoside is obtained from *Centella* (such as *Centella asiatica*), *Siegesbeckia*, or both combined. *Asiaticoside* may be also extracted from *Centella asiatica* and provided according to one embodiment.

In several embodiments in which *Albizia* is included in the formulation, the *Albizia* comprises a bark extract of *Albizia julibrissin*. Flower, stem and/or seed extracts may be used in some embodiments. In one embodiment, *Albizia* is used as an anti-glycation agent. Other anti-glycation agents can be used in addition to or instead of *Albizia*, including but not limited to polyphenols, anthocyanins and alkaloids. Examples include, for example, aminoguanidine, retinol, niacinamide, cinnamon, clove, ginger, green tea, and blueberry extracts.

In several embodiments in which algin is included in the formulation, the algin is obtained from seaweed (e.g., brown seaweed, white kelp). In some embodiments, instead of or in addition to algin, marine algae, kelp, dried seaweed or other seaweed extract is used. As with the other ingredients disclosed herein, the salt or acid form can be used in some embodiments. In one embodiment, algin is obtained by digesting seaweed in alkali and precipitating either the calcium salt or alginic acid.

In several embodiments, the formulation comprises one or more siloxanes. In several embodiments, the siloxane comprises cyclopentasiloxane. Other siloxanes are used, in several embodiments, depending on the embodiment, for example those with 4, 5, or 6 siloxane groups.

In several embodiments, the formulation comprises one or more vitamin E-based compounds. In several embodiments, the vitamin E compound comprises tocopherol, tocopheryl, tocopheryl phosphate or other derivative thereof. In several embodiments, the vitamin E compound comprises disodium lauriminodipropionate tocopheryl phosphate.

In some embodiments, triglcycerides are included in the formulation. In one embodiment, triglcycerides may be derived from coconut oil or other oils. In one embodiment, the triglycerides comprise caprylic and capric fatty acids.

According to several embodiments, zinc oxide and/or titanium dioxide are used for UV absorption. Micronized and/or nanoscale zinc oxide together with titanium dioxide can be used and can provide strong protection against ultraviolet radiation. Titanium dioxide can also be used herein as a pigment, sunscreen, sunblock and a thickener. Other oxides, dioxides or sunscreens can be used in addition to or instead of zinc oxide and/or titanium dioxide in alternate embodiments. In several embodiments, the formulation can have an SPF between 5 SPF and 100 SPF. In some embodiments, the topical composition can have an SPF of 15, 20, 25, 30, 35, 40, 45, 50, 60, 70, 80, 90, 100, and ranges in between. A physical sunscreen with an SPF of 35 is provided in several embodiments. Although a physical sunscreen is preferred, in one embodiment, the formulation contains a chemical sunscreen or does not contain sunscreen (which may be optionally provided separately).

In one embodiment, the water used in the formulation is one or more of distilled, deionized, and/or sea water.

In one embodiment, a thickener or viscosity increasing agent is provided in a range of about 0.1-15% of the total formulation (e.g., 0.1%, 0.5%, 1%, 2%, 3%, 4%, 5%, 10%, 12%, 15%, and ranges in between). In one embodiment, the percentages provided are % m/m or % w/w.

In several embodiments, the formulation comprises a stabilizer, suspending agent and/or thickener. Dimethicone crosspolymer can be used herein as a stabilizing or a suspending agent or a thickener. Types of dimethicone crosspolymers that can be used as a stabilizing agent, suspending agent or a thickener include, but are not limited to, silicone, dimethicone crosspolymer and cyclopentasiloxane, dimethicone crosspolymer 3, dimethicone crosspolymer PEG-8, cetyl dimethicone/dimethicone cross polymer, and dimethicone/vinyl dimethicone crosspolymer, and combinations thereof.

In several embodiments, a dispersing agent is used to achieve a more even distribution (and stabilization, in some embodiments) of solid particles, like pigments and fillers, throughout the formulation. In several embodiments, dimethicone, silica and polyhydroxystearic acid are used as dispersing agents. In another embodiment, disteardimonium hectorite may be used.

The topical formulations described herein may be used as a primer, foundation, or concealer in addition to reducing wrinkles, laxity and dark patches. Body and facial (e.g., eye) creams, lotions, gels, serums and other topical skin care preparations are provided in several embodiments.

In some embodiments, the formulations described herein are embedded onto a substrate. The substrate may be pre-shaped to surround the eye. A user places the substrate on his or her face and the formulation is provided directly to the eye area. This can be left on for minutes, hours or even overnight. In one embodiment, the substrate is silicone (e.g., medical grade silicone) that additionally reduces fine lines and wrinkles. Such substrates can also be pre-shaped to fit the nasolabial folds, marionette lines and other areas. In one embodiment, the formulation and substrate (e.g., the silicone pads) are provided separately in a kit.

According to several embodiments, the ingredients may be delivered in a single formulation or separately. For example, the ingredients (or groups of ingredients) may be provided in separate compositions that are co-located in a multi-chamber dispenser. In several embodiments, a kit comprising a formulation as described herein is provided along with instructions for use. In one embodiment, the kit further comprises a separate sunscreen to be reapplied on a more frequent basis (such sunscreen can be provided as a brush-on sunscreen). Applicators (brushes, sticks, sponges, etc.) may be provided to apply the formulations described herein. In one embodiment, at least one of the following is included in a kit along with the formulation: a mascara, an eyeshadow, a brow shaper, a brow color, eye liner, a highlighter, a mascara and an eyelash curler.

Several embodiments of the formulations are particularly advantageous because they provide coverage (e.g., color, camouflage) in a formulation that goes on smoothly and is not chalky or sticky. This is helpful to immediately cover areas of darker or discolored areas, while the formulation is simultaneously working on a long-term basis to reduce said darker or discolored areas (such as dark circles around the eyes). This is also helpful to minimize the number of products a user applies to his/her face (or body) because it reduces the need for a separate foundation. A beige/peach formulation is provided to counteract discoloration in some embodiments. A clear formulation (such as a serum) is provided in other embodiments.

Several embodiments of the formulations are water resistant. In one embodiment, the formulation is water resistant, e.g., with respect to SPF, for up to 30, 40, 60 and 120 minutes. Long-wear formulations are provided in several embodiments. In some embodiments, one or more mild keratolytic agents may be optionally included, wherein the keratolytic is gentle enough to be used on delicate skin. This may be helpful for crow's feet, nasolabial folds, marionette lines, or other regions on the face and body. Mild keratolytic agents may help remove or soften older, damaged surface tissue and promote the generation of new skin cells. Mild keratolytic agents used in the formulations described herein include but are not limited to one or more of the following: plant extracts (such as from the aster family), retinol, salicylic acid, alpha hydroxy acid, beta hydroxy acid, sulfur, azelaic acid, glycolic acid, urea, lactic acid, resorcinol, allantoin, fruit acids, and fruit oils. Gentle exfoliants include chemical or mechanical exfoliants. The keratolytic agents are provided, in several embodiments, in a range of about 0.005% to about 10% (e.g., 0.005%, 0.05%, 0.1%, 0.5%, 1%, 5%, 10%, and ranges in between).

In some embodiments, the formulation comprises or consists essentially of one or more of the following active ingredients: titanium dioxide, zinc oxide, *Albizia*, darutoside, *Dunaliella*, algin, *Ascophyllum, Asparagopsism*, betaine, and *Tremella* (including for example, extracts, components or portions thereof). In one embodiment, one or more additional active agents are included, such as caffeine, vitamin C, vitamin K, squalene, and/or *arnica*. Chilled or heated formulations may be provided in addition to room temperature. Chilling may aid in puffiness reduction while heating may aid in absorption.

In several embodiments, the formulations provided herein further comprise one or more seaweed, algae, fungal or other extracts. In several embodiments, the extract is extracted from the cell wall, leaf, root, bark, flower or other part of the organism. For example, although *Albizia julibrissin* bark (including an extract hereof) is used in some embodiments, leaf, stem, seed, and/or root portions are used in other embodiments.

In several embodiments, extracts of the ingredients disclosed herein are used. For example, extracts of *Albizia*, darutoside, *Dunaliella*, algin, *Ascophyllum, Asparagopsism*, and *Tremella* are used in several embodiments. An extract may be obtained, for example, by the technique of extraction or by in vitro plant cell culture.

The agents, ingredients and compounds described herein may be modified natural substances (e.g., isolates, extracts, purified, processed, chemically modified, etc.) or synthetic substances. Methods of using unique combinations of natural substances are also provided. To Applicant's knowledge, several combinations of ingredients disclosed herein represent unique enhanced formulations that are not naturally occurring (e.g., not found in nature in such combination). Moreover, in several embodiments, the individual ingredients may be modified to be structurally and/or functionally different than the naturally-occurring species, thereby resulting in markedly unique effects. Salts and acids of the ingredients identified herein, as applicable, can be used in some embodiments.

In several embodiments, the invention comprises a method of treating skin (such as the eye) using any one of the formulations described above or below. The use of any of the formulations described herein for treating skin (e.g., reducing the appearance of fine lines, laxity, wrinkles, puffiness) and/or improving skin appearance is provided in several embodiments. Several embodiments also include instructing the method or use of the formulation (e.g., via instructions for use).

Formulations for Treating Hyperpigmentation

Despite the large number of cosmetic formulations on the market, there remains a need for a cosmetic formulation that simultaneously reduces hyperpigmentation in a multi-modal manner and offers significant physical UVA and UVB sun protection, and optionally provides coverage (e.g., color) in a formulation that goes on smoothly and is not chalky or sticky. In many embodiments, the reduction of inflammation through the inclusion of an anti-inflammatory agent (e.g., vitamin E compounds) synergistically works with the other ingredients to counter hyperpigmentation via multiple pathways to enhance lightening and/or brightening effects.

Several embodiments of the present invention meet the need recited above. Several embodiments relate to unique skin care formulations for treating and protecting skin, including preventing further damage. Both healthy skin and damaged skin can benefit from several of the formulations described herein. Damaged skin can include skin with hyperpigmentation. Several embodiments are particularly useful for reducing specific regions of hyperpigmentation, thereby producing a brightening or lightening effect. An enhanced glow or radiance is achieved by several embodiments. Several formulations described herein are not limited to skin with hyperpigmentation. Indeed, many formulations are not only protective (for example by including a sun protection factor or SPF), but also nourish the skin, increase hydration and improve overall appearance, texture and firmness. Thus, several formulations of the invention are beneficial for skin that is aged, sun-damaged, wrinkled, lax, and/or blemished. Formulations according to several embodiments can be used anywhere on the body, and are especially beneficial for the face, neck, décolletage and hands, where hyperpigmentation and signs of aging may be particularly prominent.

In some embodiments, the invention comprises a topical formulation for treating and protecting skin in a subject, wherein the topical formulation is a liquid (such as a serum, lotion, liquid primer or cream), a gel, a spray, a powder, or a combination thereof. In some embodiments, the hyperpigmentation, brightening, and/or lightening formulations are used during or after a dermatological procedure (including but not limited to brow lifts, blepharoplasty, botulin and other neurotoxins, facials, fillers, dermabrasion, microdermabrasion, micro-needling, peels, exfoliations, suctioning, fluid delivery, acid treatments, massage, extractions, energy-based and other treatments, such as lasers, thermal, radiofrequency, light (e.g., photofacials/IPL), etc.).

In several embodiments, use of the formulations described herein reduces hyperpigmentation by about 10-100% (e.g., about 10%, 25%, 50%, 75%, 100% and ranges in between) after use. For example, significant lightening effects and improvements in pore size, fine lines, overall appearance, radiance, skin smoothness, and/or skin tone (evenness) are visible in several embodiments after 4 weeks, 8 weeks or 12 weeks. Certain improvements in skin may be visible or felt upon use or within days of use. Although specific regions of hyperpigmentation (e.g., age spots) are treated according to several embodiments, an overall lightening or brightening effect can also be achieved on skin that has no discrete regions of hyperpigmentation.

The topical formulation, in several embodiments, comprises or consists essentially of one or more anti-melanin agents (such as tyrosine inhibitors), one or more anti-inflammatory agents, and one or more sun protection agents. The anti-melanin agent(s) (such as tyrosine inhibitors) and anti-inflammatory agent(s) (such as vitamin E compounds) work synergistically together in many embodiments to counter undesired pigmentation.

In several embodiments, the formulation comprises (i) a first anti-melanin agent, (ii) a second anti-melanin agent, (iii) an anti-inflammatory agent, (iv) a sun protection agent, and (v) an optional anti-oxidant. In several embodiments, the formulation comprises about 0.05-5% of a first anti-melanin agent, about 0.005-5% of a second anti-melanin agent, about 0.05-5% of an anti-inflammatory agent, about 5-30% of a sun protection agent, and about 1-5% of an optional antioxidant, wherein the ranges are provided as % m/m, % m/v, or % v/v of the formulation. In some embodiments, the first anti-melanin agent comprises a *bidens pilosa* extract, the second anti-melanin agent comprises a *rheum rhaponticum* extract, the anti-inflammatory agent comprises a Vitamin E compound, the sun protection agent comprises zinc oxide and titanium dioxide offering a high sun protection factor (e.g., of SPF 30, 50 or more), and the antioxidant comprises a *thermus thermophillus* ferment extract. The formulation may additionally comprise some (e.g., 1-4) or all of the following oils in some embodiments: an *Elaeis Guineensis* oil, a *Gossypium Herbaceum* seed oil, a *Linum Usitatissimum* seed oil, a *Citrus Paradisi* seed extract, and a *Fusanus Spicatus* wood oil. In several embodiments, effective (e.g., therapeutic amounts) of ingredients are included in the formulation. An effective (e.g., therapeutic) amount, in one embodiment, may be that which reduces hyperpigmentation or uneven skin tone after at least 1-18 months (e.g., 4-12 weeks) of twice daily use.

In several embodiments, the formulation comprises a *bidens pilosa* extract, an acetyl *rheum rhaponticum* root extract, a Vitamin E compound, a *thermus thermophillus* ferment extract, a zinc oxide, and a titanium dioxide, wherein the formulation provides a high sun protection factor of SPF 30, 50 or more. In some embodiments, the formulation comprises about 0.005-5% or about 0.05-5% *bidens pilosa*, about 0.005-5% or about 0.05-5% acetyl *rheum rhaponticum* root extract, about 0.05-5% Vitamin E compound, about 0.05-10%, about 5-15% zinc oxide, and about 10-15% titanium dioxide, wherein the ranges are provided as % m/m, % m/v, or % v/v of the formulation. In many embodiments, the percentages provided are % m/m or % w/w.

In several embodiments, the *rheum rhaponticum* extract comprises acetyl *rheum rhaponticum* root extract and the vitamin E compound comprises disodium lauriminodipropionate tocopheryl phosphates. The formulation may be a topical formulation in the form of e.g., a liquid, cream or gel, and in one embodiment is a paraben-free facial primer.

In several embodiments, a method of treating skin discoloration is provided, the method comprising identifying at least one region of a skin tissue having discoloration or an uneven tone (including but not limited to hyperpigmentation) and applying, or instructing application of, any one of the topical formulations described herein to the skin region, wherein the formulation lightens the hyperpigmentation and/or improves skin tone uniformity, as well as provides protection from ultraviolet rays, In some embodiments of the invention, the anti-melanin agents used herein directly and/or indirectly reduce the production of melanin, degrade melanin, reduce the melanin transfer from melanocytes to keratinocytes, and/or reduce the storage of melanin. In some embodiments, anti-melanin agents are tyrosinase inhibitors that inhibit the production and/or accumulation of melanin by inhibiting tyrosinase (which facilitates melanogenesis). Tyrosinase inhibitors used in the formulations described herein include but are not limited to one or more of the following: extracts from the rhubarb family (such as *rheum rhaponticum*, acetyl *rheum rhaponticum* root extract), ascorbic acid, bearberry, licorice, mulberry, kojic acid, green tea (epicatechin gallate, epigallocatechin gallate and gallocatechin gallate) and acetylated hydroxystilbene. Tyrosinase inhibitors used in the formulations described herein also include but are not limited to polyphenols such as curcuminoids, flavonoids (e.g., anthocyanins, flavanols, flavanones, flavonols, flavones, isoflavones) and stilbenoids (e.g., resveratrol, pterolstilbene), free radical scavengers, and copper chelators. Anti-melanin agents used in the formulations described herein include tyrosinase inhibitors, as well as other agents that are not tyrosinase inhibitors but also have an ability to reduce the production of melanin, degrade melanin and/or reduce the storage of melanin (e.g., endothelin inhibitors). In some embodiments, the anti-melanin agent is a tyrosinase inhibitor comprising a *rheum rhaponticum* extract (e.g., acetyl *rheum rhaponticum* root extract) and a panthenol compound (e.g., panthenyl triacetate). In some embodiments, the anti-melanin agent is acetylated hydroxystilbene. The anti-melanin agents are provided, in several embodiments, in a range of about 0.001% to about 10% (e.g., 0.001%, 0.01%, 0.03%, 0.05%, 0.1%, 0.5%, 1%, 5%, 10%, and ranges in between) % m/m, % m/v, or % v/v in the formulation. In many embodiments, the percentages provided are % m/m or % w/w. In some embodiments, the panthenol compound (e.g., panthenyl triacetate) acts as an anti-irritant and anti-inflammatory. As discussed herein, reducing inflammation may reduce hyperpigmentation through an inflammatory-mediated pathway.

In several embodiments, at least two types of anti-melanin agents are included in a formulation. For example, one type reduces the production of melanin, while the other type(s) degrades (or enhance the degradation of) melanin, reduces the melanin transfer from melanocytes to keratinocytes, and/or reduces the storage of melanin. The use of at least two different anti-melanin agents provides synergistic effects in several embodiments. For example, in one embodiment, the formulation contains a *bidens pilosa* extract as an anti-melanin agent to beneficially affect melanin transport as well as a *rheum rhaponticum* extract (e.g., acetyl *rheum rhaponticum* root extract) as a tyrosinase inhibitor. These two extracts are combined with one or more anti-inflammatories and sun protection agents in many embodiments of the formulation to accomplish a multi-modal approach to effectively address the appearance of skin discoloration (e.g., hyperpigmentation, hypopigmentation, etc.). By affecting different points in the cascade of event that leads to discoloration, several embodiments of the formulation as described herein are particularly advantageous.

In some embodiments of the invention, the anti-inflammatory agents decrease redness and irritation (such as that caused by UV exposure) and fortify resistance to inflammation. The anti-inflammatory agents may have antioxidant properties by reacting with reactive oxygen species. The anti-inflammatory agents may also absorb the energy from UV light and are photo-protective, and reduce UV-induced free radical damage to skin. In several embodiments, the anti-inflammatory agents, by acting through a different pathway that involves inflammation's influence on pigmentation are particularly potent when combined with the anti-melanin agents. Post-inflammatory hyperpigmentation or hypermelanosis, which can occur after cutaneous inflammation or injury, is one example of hyperpigmentation that is related to inflammation, and according to several embodiments, is treated with the formulations described herein. Anti-inflammatory agents used in the formulations described herein include but are not limited to one or more of the following: vitamin E compounds (such as disodium lauriminodipropionate tocopheryl phosphate and other tocopherols), vitamin A compounds, vitamin B compounds, and vitamin D compounds. In several embodiments, the anti-inflammatory agent comprises a vitamin E compound (e.g., disodium lauriminodipropionate tocopheryl phosphate). The anti-inflammatory agents are provided, in several embodiments, in a range of about 0.1% to about 20% (e.g., 0.1%, 0.5%, 0.8%, 1%, 5%, 10%, 20%, and ranges in between) % m/m, % m/v, or % v/v in the formulation. In many embodiments, the percentages provided are % m/m or % w/w.

In some embodiments of the invention, the sun protection agents used have an SPF of 30, 50 or higher. In many embodiments, the sun protection agents are physical sunscreens (and not chemical sun screens) that block both UVA and UVB rays. The sun protection agents used in the formulations described herein include but are not limited to zinc oxide, titanium dioxide and other mineral oxides. The sun protection agents are provided, in several embodiments, in a range of about 2% to about 40% (e.g., 2%, 5%, 10%, 15%, 20%, 25%, 30%, 40%, and ranges in between) % m/m, % m/v, or % v/v in the formulation. In many embodiments, the percentages provided are % m/m or % w/w. In some embodiments, the formulations comprise 5-15% zinc oxide and 10-15% titanium dioxide. The terms sun protection agents, suncreens and sunblocks can be used interchangeably herein. Although physical suncreens are used in many embodiments, chemical suncreens may also be used.

In some embodiments, the formulation comprises or consists essentially of one or more anti-melanin agents (such as tyrosine inhibitors), one or more anti-inflammatory agents, and one or more sun protection agents and at least one of the following ingredients: a skin conditioning agent, a solvent, a silicone, an emollient, a preservative, a thickener, an antioxidant, and an excipient. Optional colorants and fragrances may additionally be included. Agents to adjust or balance pH may also be included.

According to several embodiments, a formulation for reducing hyperpigmentation is provided, said formulation comprising or consisting essentially of: one or more anti-melanin agents in an amount sufficient to reduce the synthesis of melanin; one or more anti-inflammatory agents in an amount sufficient to inhibit an inflammatory mediator involved in increasing melanin; and one or more agents that at least partially block ultraviolet rays. Optionally, one or more keratolytic agents in an amount sufficient to at last partially dissolve or soften the keratin is also included. In some embodiments, the ingredients act on hyperpigmentation through a different (but perhaps related) pathway and enhance the effectiveness of the formulation as a whole.

The topical formulation, in some embodiments, comprises or consists essentially of the following ingredients: about 0.05-5% (e.g., about 0.5-3%) vitamin E compound, 0.005-5% (e.g., about 0.03-3%) *rheum rhaponticum* extract (e.g., acetyl *rheum rhaponticum* root extract) and about 0.005-5% (e.g., about 0.03-3%) asteraceae extract (e.g., *bidens pilosa* extract). In addition, some or all of the following ingredients may be included: about 1-25% (e.g., about 5-30%) sunscreen and about 0.5-10% (e.g., about 1-5%) *thermus thermophillus* ferment. In addition, in some embodiments, at least one of the following ingredients is included: about 40-70% (e.g., about 50-65%) of a skin conditioning agent, about 5-20% (e.g., about 5-15%) of a solvent, such as water, about 0.5-15% (e.g., about 1-6%) of a water-resistant agent/film forming agent. Emollients, humectants, preservatives, thickeners, binders, colorants, stabilizers, anti-foaming agents, and/or fragrances may additionally be included in the range of about 0.1-25%. In many embodiments, the percentages provided are % m/m or % w/w.

In several embodiments, the invention comprises or consists essentially of several or all of the following agents (or their respective derivatives, esters, acids, salts, and alcohols): one or more oxides or dioxides (e.g., titanium dioxide, zinc oxide, and/or iron oxide), one or more silicon/siloxane/silicone-based compounds (e.g., cyclopentasiloxane, dimethicone, dimethicone crosspolymer, trimethylsiloxysilicate, dimethicone/vinyl dimethicone crosspolymer, dimethiconol, and/or triethoxycaprylylsilane), one or more solvents (e.g., water), one or more triglycerides (e.g., caprylic/capric triglycerides), one or more bacterial, plant and/or fruit extracts (e.g., *thermus thermophillus* ferment, *rheum rhaponticum* extract such as acetyl *rheum rhaponticum* root extract, grapefruit seed extract, aster plant extract such as *bidens pilosa* extract, and/or *vanilla planifolia* fruit extract), one or more vitamin-based compounds such as panthenol, vitamin-E or vitamin-C based compounds (e.g., disodium lauriminodipropionate tocopheryl phosphates, tocopherol, tocotrienols, vitamin E, ascorbic acid, panthenol, and/or panthenyl triacetate), one or more oils (e.g., *fusanus spicata* wood oil, *elaeis guineensis* oil, *gossypium herbaceum* seed oil, *linum usitatissimum* seed oil), and one or more glycerin-based compounds (e.g., glycerin and/or glyceryl isostearate). Additionally, emulsifiers, surfactants and preservatives can be included (e.g., polyhydroxystearic acid, phenoxyethanol, potassium sorbate, dehydroacetic acid, and/or benzoic acid). Film formers may be used (such as acrylates, including acrylates/C12-22 alkyl methacrylate copolymer). Isocetyl stearoyl stearate may be used in some embodiments as a skin conditioning agent. Propylene or pentylene glycol (or other glycol) may be included as, for example, a humectant and/or solvent. Thickeners such as cellulose compounds (e.g. methylcellulose) may be included. Ascorbic acid may function as a pH adjuster in some embodiments.

Although preservatives are provided in certain embodiments, the formulations described herein can be manufactured with reduced or no synthetic preservatives. In some embodiments, the formulations are free of one or more of the following: parabens, phthalates, sulfates, mineral oil, gluten, allergens, and irritants.

In several embodiments, the formulation comprises or consists essentially of Titanium Dioxide, Zinc Oxide, Cyclopentasiloxane, Isocetyl Stearoyl Stearate, Dimethicone Crosspolymer, *Thermus Thermophillus* Ferment, Water/Aqua/Eau, Dimethicone/Vinyl Dimethicone Crosspolymer, Disodium Lauriminodipropionate Tocopheryl Phosphates, Panthenyl Triacetate, Acetyl *Rheum Rhaponticum* Root Extract, *Bidens Pilosa* Extract, *Elaeis Guineensis* (Palm) Oil, *Gossypium Herbaceum* (Cotton) Seed Oil, *Linum Usitatissimum* (Linseed) Seed Oil, Tocopherol, Dimethiconol, *Citrus Paradisi* Seed Extract, Glycerin, Dimethicone, *Fusanus Spicatus* Wood Oil, *Vanilla Planifolia* Fruit Extract, Ascorbic Acid, Caprylic/Capric Triglyceride, Propylene Glycol (or pentylene glycol or other glycol), Triethoxycaprylylsilane, Acrylates/C12-22 Alkyl Methacrylate Copolymer, Phenoxyethanol, Benzoic Acid, Dehydroacetic Acid, Potassium Sorbate, and Iron Oxides (CI 77491, CI 77492, CI 77499). Methylparaben may optionally be included, although in several embodiments, the formulation is free of methylparaben and/or other parabens. Farnesol may optionally be included, although in several embodiments, the formulation is free of farnesol, or fragrance, free.

The use of agents, ingredients and compounds may be used interchangeably herein. Reference to the term "based" includes the recited agent, ingredient or compounds. For example, a panthenol-based compound includes panthenol itself. The terms composition and formulation can be used interchangeably. Where percentages are provided for agents, ingredients and compounds, they can be % m/m, % m/v or % v/v with respect to the formulation as a whole, unless otherwise indicated, The agents, ingredients and compounds described herein may be modified natural substances (e.g., isolates, extracts, purified, processed, chemically modified, etc.) or synthetic substances. Methods of using unique combinations of natural substances are also provided.

In several embodiments, the invention comprises a method of treating skin using any one of the formulations described above or below. The use of any of the formulations described herein for treating skin (e.g., reducing hyperpigmentation) and/or improving skin appearance is provided in several embodiments. Several embodiments also include instructing the method or use of the formulation (e.g., via instructions for use).

As described above, several embodiments of the present invention relate to unique skin care formulations for treating and protecting skin. The formulations described herein can be beneficial for both healthy and damaged skin. In several embodiments, use of the formulations described herein provides one or more of the following advantages: (i) reduction in the appearance of redness, (ii) reduction in hyperpigmentation (e.g., reduction in age spots, discolored scar tissue, birthmarks, or other discoloration), (iii) skin looks and feels smoother; (iv) increased firmness, (v) increased hydration, (vi) improved skin tone and texture (e.g., increased evenness), (vii) clearer complexion, (viii) improved radiance, (ix) fine lines, pores, and wrinkles appear less visible, (x) improved overall appearance of skin, (xi) reinforcement of the skin's natural defenses, and (xii) improved epidermal structural integrity. Advantageously, in several embodiments, these improvements are obtained with formulations that are gentle and non-irritating, with no or little erythema, edema, dryness, peeling, itching, stinging, tingling, or burning sensation. Because undesired effects are nominal or nonexistent, the formulation fosters regular use by a subject, which enables longer term improvements in skin characteristics.

The formulations described herein can provide both short-term and long-term benefits according to several embodiments. Beneficial effects from use of the formulations described herein occur upon use, within hours of use, within 1-2 days, 3-4 days, about 7 days, about 14 days, or within about 3 weeks. In several embodiments, the skin characteristics continue to improve over about 2-4 weeks, about 4-6 weeks, about 6-10 weeks, or about 12-16 weeks of use.

Several embodiments of the invention comprise a formulation for protecting against UV damage and reinforcing the skin's natural defenses. In some embodiments, the formulation is in a liquid, gel or powder form. The formulations described herein can be applied prior to or after foundation or other make-up. In some embodiments, the formulation is colorless; however, in other embodiments, the formulation contains sufficient color to serve as foundation or cover-up. In some embodiments, the pH of the formulations is slightly basic, slightly acidic or neutral. In some embodiments, a pH of 3-5, 4-6, 5-7, 6-8, or ranges in between, are provided. Lower or higher pH values may also be used.

The formulations described herein have one or more of the following uses: primer, moisturizer, sunscreen, setting mist, and color (cover-up, coverage, or foundation). The unique aspects of many of the formulations described herein provide a multi-functional product that blends skin care and sun care, and offers a high SPF primer, color coverage, skin nourishment, anti-oxidants and a lightening effect (e.g., through a reduction of discoloration or pigmentation).

According to several embodiments, the formulations described herein can be applied by hand, by sponge, by spraying, by applicator, by brush, or through use of a composition-impregnated wipe or tissue. In some embodiments, the formulations are absorbent (e.g., readily absorbable) such that no separate means are needed to enhance absorption. However, in some embodiments, low frequency ultrasound, massage, application of an electrical field, mechanical manipulation or vibration may be used to facilitate absorption. In some embodiments, the formulation is useful post-surgery or dermatological treatment, where, for example, discoloration, may be an issue. Several topical formulations herein described can penetrate top layers of the skin. Further, some of the formulations described herein may be suitable for use for application under one or more skin layers (e.g., as an injectable).

The invention, according to several embodiments, comprises a topical formulation (such as an SPF liquid primer) for treating skin that includes *rheum rhaponticum* and asteraceae. In one embodiment, the *rheum rhaponticum* comprises acetyl *rheum rhaponticum* extract, extracted from the leaf, root, flower or other part of the plant. In one embodiment, the asteraceae comprises *bidens pilosa* extract from the leaf, root, flower or other part of the plant. *Rheum rhaponticum* and *bidens pilosa* are unrelated compounds that Applicant believes have unexpected synergistic effects in combination to reduce hyperpigmentation or otherwise treat skin. In addition to extracts of *rheum rhaponticum* and *bidens pilosa*, both vitamin E compounds and sunscreen are included in some embodiments. Vitamin E compounds, again unrelated to *rheum rhaponticum* and *bidens pilosa*, are believed to contribute synergistically with *rheum rhaponticum* and *bidens pilosa* for the treatment of skin, including the reduction of hyperpigmentation. For example, the synergistic combination of *rheum rhaponticum*, *bidens pilosa* and an anti-inflammatory agent (such as a Vitamin E compound) in some embodiments, decreases melanin synthesis, decreases accumulation of melanin in keratinocytes, and reduces inflammation and redness. Further, in some embodiments, the combination of an anti-melanin agent, such as a tyrosinase inhibitor, and Vitamin E compounds or other anti-inflammatory agents synergistically decreases melanin synthesis, decreases accumulation of melanin in keratinocytes, and reduces inflammation and redness. In some embodiments, the *rheum rhaponticum* and the *bidens pilosa* are provided in the range of about 0.0005-10% and the vitamin E is provided in the range of about 0.05-10%. Sunscreen may be provided in the range of about 1-35%. Sunscreen provides an additional benefit by shielding the regions of hyperpigmentation from further pigmentation during the treatment process, thus facilitating the therapeutic benefits of the formulation. Further, sunscreen reduces the incidence of future hyperpigmentation and damage. In some embodiments, *thermus thermophillus* (e.g., *thermus thermophillus* ferment) is included with extracts of *rheum rhaponticum* and *bidens pilosa* and optionally Vitamin E compounds, sunscreen, and other ingredients. The *thermus thermophillus*, which is unrelated to *rheum rhaponticum*, *bidens pilosa* and vitamin E, is believed to provide further synergistic benefits to the combination of *rheum rhaponticum* and *bidens pilosa* (and optionally Vitamin E compounds). For example, *thermus thermophillus*, in some embodiments, acts as an antioxidant that is activated by heat and/or light thereby protecting against UV damage, which in turns preserves and reinforces the skin's natural defenses and improves epidermal structural integrity. *Thermus thermophillus* may also work as an anti-oxidant to supplement the vitamin E compound's ability to reduce inflammation, thereby reducing the effect of inflammation on increased pigmentation (e.g., through inflammatory mediators). To Applicant's knowledge, several combinations of ingredients disclosed herein represent unique formulations that are not naturally occurring (e.g., not found in nature in such combination). Moreover, in several embodiments, the individual ingredients are modified so as to be structurally and/or functionally different than the naturally-occurring species, thereby resulting in markedly unique effects.

In addition, in some embodiments, at least one of the following ingredients is included: a skin conditioning agent, a solvent, a silicone, an emollient, a preservative, a thickener, an antioxidant, an anti-inflammatory agent, and an excipient. Colorants and fragrances may additionally be included. In some embodiments, the formulation further includes one or more of the following: amino acids, peptides, phospholipids, additional vitamins, growth factors, and additional anti-aging compounds. Surfactants, gelling agents, and pH balancers may also be included.

In several embodiments, the formulation comprises a combination of various combination groups and individual ingredients. In some embodiments, the formulation comprises, consists essentially of or consists of several or all of the following groups of ingredients (or in certain cases of water and sandalwood, single ingredients):

TABLE 4

| Group | Agent/Ingredient |
| --- | --- |
| 4.1 | cyclopentasiloxane, dimethicone crosspolymer, dimethicone/vinyl dimethicone crosspolymer, and dimethiconol; |
| 4.2 | zinc oxide and triethoxycaprylylsilane; or zinc oxide, caprylic/capric triglyceride, glyceryl isostearate, and polyhydroxy stearic acid; |
| 4.3 | isocetyl stearoyl stearate or distilled water; |
| 4.4 | acrylates/C12-22 alkyl methacrylate copolymer, water, and a glycol (such as propylene or |

TABLE 4-continued

| Group | Agent/Ingredient |
|---|---|
| | pentylene glycol); or cyclopentasiloxane and trimethylsiloxysilicate; |
| 4.5 | thermus thermophillus ferment, glycerin, phenoxyethanol, and potassium sorbate; |
| 4.6 | titanium dioxide and dimethicone; |
| 4.7 | disodium lauriminodipropionate tocopheryl phosphates, water, phenoxyethanol, dehydroacetic acid, and benzoic acid; |
| 4.8 | panthenyl triacetate and acetyl rheum rhaponticum root extract |
| 4.9 | bidens pilosa extract, elaeis guineensis (palm) oil, gossypium herbaceum (cotton) seed oil, linum usitatissimum (linseed) seed oil, tocopherol; |
| 4.10 | grapefruit seed extract, glycerin, ascorbic acid |
| 4.11 | iron oxides (Cl 77491, Cl 77492, Cl 77499) and triethoxycaprylylsilane; |
| 4.12 | santalum spicatum (sandalwood); |
| 4.13 | caprylic/capric triglyceride and vanilla planifolia fruit extract |

In several embodiments, effective (e.g., therapeutic) amounts of active ingredients are provided in the formulation. In many embodiments, the percentages provided are % m/m or % w/w.

In one embodiment, group (4.1) above is provided in a range of about 30-80% (e.g., 30%, 50%, 60%, 70%, 80% and ranges in between) of the total formulation, with individual ranges (with respect to percentage amount vis-à-vis the select group of the following ingredients) as follows: siloxanes such as cyclopentasiloxane (about 30%, 45%, 50%, 70%, 75% 80%, 82%, 85%, 90%, and ranges in between), dimethicone crosspolymer (about 6%, 8%, 10%, 12%, 14%, 20%, and ranges in between), dimethicone/vinyl dimethicone crosspolymer (about 1%, 2%, 3%, 6%, 10%, and ranges in between) and dimethiconol (about 0.1%, 0.5%, 1%, 2%, 5%, and ranges in between). By way of example, if cyclopentasiloxane is provided at 80% vis-à-vis the select group of compounds listed in group (4.1), and group (4.1) is provided as 60% of the total formulation, then cyclopentasiloxane will be present as 48% of the total formulation. In several embodiments, group (4.1) can further include or be substituted with elastomers, such as high molecular weight silicone elastomers, decamethylcyclopentasiloxane, phenyl silicons, alkylmethylsiloxanes, polydimethylsiloxanes, cross-linked silicone elastomer dispersions, hexamethyldisolixane, cyclomethicone, and trimethylsilyamodimethicone, and combinations thereof. In several embodiments, group (1) can be a gel and be used in conditioning the skin, as well as for sebum absorption.

In one embodiment, group (4.2) and group (4.6) above are provided in a range of about 3-20% (e.g., 3%, 4%, 5%, 10%, 15%, 20%, and ranges in between) of the total formulation for group (4.2) and 0.5-25% (e.g., 0.5%, 1%, 2%, 3%, 5%, 10%, 15%, 20%, 25%, and ranges in between) of the total formulation for group (4.6). Individual ranges (with respect to percentage amount vis-à-vis the select group of the following ingredients) can be as follows for group (4.2): zinc oxide (about 20%, 30%, 40%, 50%, 60%, 70%, and ranges in between), caprylic/capric triglyceride (about 20%, 35%, 45%, 55%, 65%, 75%, and ranges in between), glyceryl isostearate (about 1%, 2%, 4%, 6%, 8%, and ranges in between) and polyhydroxy stearic acid (about 0.5%, 1%, 2%, 5%, and ranges in between). Alternatively, zinc oxide and triethoxycaprylylsilane are used instead. These two ingredients are used in the following amounts in several embodiments: zinc oxide (about 2%, 4%, 8%, 10%, 12%, 15%, 20%, and ranges in between) and triethoxycaprylylsilane (about 0.1%, 0.3%, 0.5%, 1%, 2%, 3%, and ranges in between). Individual ranges (with respect to percentage amount vis-à-vis the select group of the following ingredients) can be as follows for group (4.6): titanium dioxide (50, 60, 70, 80, 95, 96, 97, 98, 99%, and ranges in between) and dimethicone (about 1%, 2%, 4%, 6%, 8%, and ranges in between). According to several embodiments, zinc and titanium dioxide are used for UV absorption. Micronized and/or nanoscale zinc oxide together with titanium dioxide can be used and can provide strong protection against ultraviolet radiation and can be used in sunscreen, sunblock, tanning, and sun tanning lotions, creams, gels, and liquids according to several embodiments. Titanium dioxide can also be used herein as a pigment, sunscreen, sunblock and a thickener. Other ingredients that can be used in addition to or as a substitute for the ingredients in group (4.2) or (4.6) include but are not limited to, 4-methylbenzylidene camphor (Enzacamene, Parsol 5000, Eusolex 6300, MBC), Tinosorb M (bisoctrizole, methylene bis-benzotriazolyl tetramethylbutylphenol, MBBT), Tinosorb S (Bis-ethylhexyloxyphenol methoxyphenol triazine, bemotrizinol, BEMT, anisotriazine), Meroyl XL, (drometrizole trisiloxane), Benzophenone-9 (Uvinul DS 49, CAS 3121-60-6, Sodium Dihydroxy Dimethoxy Disulfobenzophenone), Uvinul T 150 (Octyl triazone, ethylhexyl triazone, EHT), Uvinul A Plus (Diethylamino Hydroxybenzoyl Hexyl Benzoate), Uvasorb HEB (Iscotrizinol, Diethylhexyl butamido triazone, DBT), Parsol SLX (Dimethico-diethylbenzalmalonate, Polysilicone-15), and Isopentenyl-4-methoxycinnamate (Isoamyl p-Methoxycinnamate, IMC, Neo Heliopan E1000, Amiloxate). In some embodiments, the formulations comprise 5-15% zinc oxide and 10-15% titanium dioxide.

In one embodiment, ingredient (4.3) above, water (e.g., distilled water), is provided in a range of about 1-20% (e.g., 1%, 2%, 3%, 4%, 5%, 10%, 12%, 15%, 20%, and ranges in between) of the total formulation. Alternatively, isocetyl stearoyl stearate is used instead or in addition to water in a range of about 5-20% (e.g., 5%, 10%, 12%, 15%, 20%, and ranges in between).

In one embodiment, group (4.4) above is provided in a range of about 0.5-10% of the total formulation (e.g., 0.5%, 1%, 2%, 3%, 4%, 5%, 6%, 10%, and ranges in between), with individual ranges (with respect to percentage amount vis-à-vis the select group of the following ingredients) as follows: cyclopentasiloxane (about 20%, 30%, 40%, 50%, 60%, 70%, and ranges in between) and trimethylsiloxysilicate (about 20%, 30%, 40%, 50%, 60%, 70%, and ranges in between). Alternatively, group (4.4) above is provided in a range of about 0.5-10% of the total formulation (e.g., 0.5%, 1%, 2%, 3%, 4%, 5%, 6%, 10%, and ranges in between), with individual ranges (with respect to percentage amount vis-à-vis the select group of the following ingredients) as follows: acrylates/C12-22 alkyl methacrylate copolymer (about 20%, 30%, 40%, 50%, 60%, 70%, and ranges in between), water (about 20%, 30%, 40%, 50%, 60%, 70%, and ranges in between), and a glycol, such as propylene or pentylene glycol (about 1%, 2%, 3%, 4%, 5%, 10%, and ranges in between).

In one embodiment, group (4.5) above is provided in a range of about 0.5-10% of the total formulation (e.g., 0.5%, 1%, 2%, 3%, 4%, 5%, 6%, 10%, and ranges in between), with individual ranges (with respect to percentage amount vis-à-vis the select group of the following ingredients) as follows: *thermus thermophillus*, such a *thermus thermophillus* ferment, (about 80%, 85%, 90%, 94%, 95%, 97%, 98%, 99%), glycerin (about 2%, 3%, 4%, 5%, 6%, 10%, and ranges in between), phenoxyethanol (about 0.1%, 0.5%, 1%, 2%, 5%, and ranges in between), and potassium sorbate (about 0.01%, 0.05%, 0.1%, 1%, 5%, and ranges in between). *Thermus thermophillus* can, according to several embodiments, function as an antioxidant activated by heat and light, to protect against UV damage, to preserve and reinforces the skin's natural defenses, and to improve epidermal structural integrity. *Thermus thermophillus* ferment is a product of the fermentation of *thermus thermophillus* and is one non-limiting example of the *thermus* genus than can be used herein. Other species include but are not limited to *T. antranikianii, T. aquaticus, T. brockianus, T. caldophilus, T. filiformis, T. igniterrae, T. kawarayuensis, T. nonproteolyticus, T. oshimai, T. rehai, T. scotoductus, T. yunnanensi*, and *T. manikaranii*. Fermented or non-fermented alternatives can be used.

In one embodiment, group (4.7) above is provided in a range of about 0.1-10% of the total formulation (e.g., 0.1%, 0.5%, 1%, 2%, 3%, 4%, 5%, 10%, and ranges in between), with individual ranges (with respect to percentage amount vis-à-vis the select group of the following ingredients) as follows: disodium lauriminodipropionate tocopheryl phosphates (about 20%, 40%, 60%, and ranges in between), water (about 20%, 40%, 55%, 59%, 65%, 70%, 80%, and ranges in between), phenoxyethanol (about 0.1%, 0.4%, 0.8%, 1.2%, 2%, 4%, and ranges in between), dehydroacetic acid (about 0.01%, 0.02%, 0.08%, 0.1%, 1%, 2%, 4%, and ranges in between), and benzoic acid (about 0.02%, 0.12%, 0.25%, 0.5%, 1%, 5%, and ranges in between). Disodium lauriminodipropionate tocopheryl phosphate serves, in several embodiments, as an antioxidant and an anti-inflammatory. In addition to, or in lieu of, disodium lauriminodipropionate tocopheryl phosphates, one or more of the following is provided: vitamin A, vitamin C, vitamin E, and beta-carotene.

In one embodiment, group (4.8) above is provided in a range of about 0.1-10% of the total formulation (e.g., 0.1%, 0.5%, 1%, 2%, 3%, 4%, 5%, 10%, and ranges in between), with individual ranges (with respect to percentage amount vis-à-vis the select group of the following ingredients) as follows: panthenyl triacetate (about 85%, 90%, 95%, 97%, 99%, and ranges in between) and acetyl *rheum rhaponticum* root extract (about 0.5%, 1%, 2%, 3%, 4%, 5%, 10%, 20%, and ranges in between). Panthenyl triacetate is an ingredient that, according to several embodiments, is used as an anti-irritant and an anti-inflammatory. It is a stable oil-soluble derivative of pantothenic acid and a member of the vitamin B complex. In several embodiments, this vitamin has soothing and anti-irritating properties on the skin, stimulates the cell proliferation and contributes to biological processes in skin metabolism. Pantothenic acid is a key molecule in Coenzyme A, an activator for many metabolic processes, and includes metabolic processes in the skin. Because of its lipophilic character, pantothenic acid is used herein in some embodiments to facilitate penetration of the formulation into the skin (e.g., via the sebaceous glands). In addition to, or in lieu of, panthenyl triacetate, other compounds related to panthenol may be used. Acetyl *Rheum rhaponticum* root extract is one non-limiting example of *rheum rhaponticum* that can be used herein to decrease melanin synthesis in melanocytes and its accumulation in keratinocytes.

In one embodiment, group (4.9) above is provided in a range of about 0.1-10% of the total formulation (e.g., 0.1%, 0.5%, 1%, 2%, 3%, 4%, 5%, 10%, and ranges in between), with individual ranges (with respect to percentage amount vis-à-vis the select group of the following ingredients) as follows: *bidens pilosa* extract (about 0.1%, 0.5%, 1%, 2% 3%, 5%, 7%, 10%, 15%, 30%, and ranges in between), *elaeis guineensis* (palm) oil (about 1%, 3%, 5%, 7%, 10%, 15%, 20%, 30%, and ranges in between), *gossypium herbaceum* (cotton) seed oil (about 1%, 3%, 5%, 7%, 10%, 15%, 20%, 30%, and ranges in between), *linum usitatissimum* (linseed) seed oil, (about 1%, 3%, 5%, 7%, 10%, 15%, 20%, 30%, and ranges in between), and tocopherol (about 1%, 3%, 5%, 7%, 10%, 15%, 20%, 30%, and ranges in between). Other species/sub-species of *elaeis, gossypium* and *linum* can also be used. Other botanical oils may be use in addition to or in lieu of the oils identified herein, including but not limited to coconut oil, walnut oil, avocado oil, castor oil, almond oil, grapeseed oil, olive oil, etc., and combinations thereof.

In one embodiment, group (4.10) above is provided in a range of about 0.01-5% of the total formulation (e.g., 0.01% 0.1%, 0.5%, 0.75%, 1%, 2%, 3%, 4%, 5%, and ranges in between), with individual ranges (with respect to percentage amount vis-à-vis the select group of the following ingredients) as follows: grapefruit seed extract such as *citrus paradisi* extract (about 2%, 4%, 6%, 8%, 10%), glycerin (about 75%, 80%, 85%, 87%, 90%, 95%, and ranges in between), ascorbic acid (about 1%, 3%, 5%, 7%, 10%, 15%, 20%, and ranges in between).

In one embodiment, (4.11) above is provided in a range of about 0.01-5% of the total formulation (e.g., 0.01% 0.1%, 0.5%, 0.75%, 1%, 2%, 3%, 4%, 5%, and ranges in between), with individual ranges (with respect to percentage amount vis-à-vis the select group of the following ingredients) as follows: iron oxides (about 90%, 95% 98%, 100%, and ranges in between) (CI 77491, CI 77492, CI 77499) and triethoxycaprylylsilane (about 1%, 2%, 3%, 4%, 5%, and ranges in between);

In one embodiment, ingredient (4.12) above, *santalum spicatum* (sandalwood), is provided in a range of about 0.001-3% (e.g., 0.001%, 0.01% 0.1%, 0.2%, 0.5%, 0.75%, 1%, 2%, 3% and ranges in between) of the total formulation. In several embodiments described herein, the formulation comprises sandalwood oil. Sandalwood oil is an essential oil that can be obtained, for example, from the steam distillation of chips and billets cut from the heartwood of the sandalwood tree. In several embodiments, sandalwood oil is used for skin conditioning. *Santalum spicatum* is one non-limiting example of sandalwood that may be used; other species of sandalwood can also be used. A combination of *fusanus spicatus* wood oil and farnesol are used in several embodiments.

In one embodiment, group (4.13) above is provided in a range of about 0.001-3% of the total formulation (e.g., 0.001%, 0.01% 0.1%, 0.5%, 0.75%, 1%, 2%, 3%, and ranges in between), with individual ranges (with respect to percentage amount vis-à-vis the select group of the following ingredients) as follows: caprylic/capric triglyceride (about 70%, 80%, 90%, 95%, and ranges in between) and *vanilla planifolia* fruit extract (about 5%, 8%, 10%, 12%, 15%, and ranges in between). Vanilla extract, such as *vanilla planifolia* fruit extract, can be used herein to give the formulations a pleasant fragrance and is one non-limiting example of a fragrance. Other fragrances can also be used, including lavender, lemon, orange, *gardenia*, jasmine, mint, and other flower and fruit extracts. Fragrance-free alternatives are also used herein.

In one embodiment, the formulation comprises or consists essentially of some or all of the following agents in the percentage ranges (vis-à-vis the formulation as a whole) provided:

TABLE 5

| Agent/Ingredient | Approximate % Amount in Formulation |
|---|---|
| Siloxane (e.g., Cyclopentasiloxane) | 3-65% (e.g., 30-60%) |
| Titanium Dioxide | 5-20% |
| Isocetyl Stearoyl Stearate | 5-20% |
| Zinc Oxide | 2-15% |
| Dimethicone Crosspolymer | 2-10% |
| Thermus Thermophillus Ferment | 1-5% |
| Water/Aqua/Eau | 1-5% |
| Dimethicone/Vinyl Dimethicone Crosspolymer | 0.5-5% |
| Iron Oxides | 0.5-5% |
| Panthenyl Triacetate | 0.1-5% |
| Acrylates/C12-22 Alkyl Methacrylate Copolymer | 0.1-5% |
| Vitamin E Compound (e.g., Disodium Lauriminodipropionate Tocopheryl Phosphates) | 0.1-5% |
| Dimethiconol | 0.1-5% |
| Glycerin | 0.05-5% |
| Dimethicone | 0.05-5% |
| Elaeis Guineensis (Palm) Oil | 0.05-5% |
| Gossypium Herbaceum (Cotton) Seed Oil | 0.05-5% |
| Citrus Paradisi (Grapefruit) Seed Extract | 0.05-5% |
| Triethoxycaprylylsilane | 0.05-5% |
| Bidens Pilosa Extract | 0.05-5% |
| Linum Usitatissimum (Linseed) Seed Oil | 0.05-5% |
| Fusanus Spicatus Wood Oil, Farnesol | 0.05-5% |
| Ascorbic Acid | 0.05-5% |
| Glycol (e.g., Pentylene or Propylene Glycol) | 0.05-5% |
| Caprylic/Capric Triglyceride | 0.05-5% |
| Phenoxyethanol | 0.01-5% |
| Rheum Rhaponticum (e.g., Acetyl Rheum Rhaponticum Root Extract) | 0.005-5% |
| Vanilla Extract (e.g., Vanilla Planifolia Fruit Extract) | 0.001-5% |
| Potassium Sorbate | 0.0005-5% |
| Benzoic Acid | 0.0005-5% |
| Dehydroacetic Acid | 0.0005-5% |
| Tocopherol | 0.0001-5% |

In many embodiments, the percentages provided are % m/m or % w/w.

In some embodiments, the groups of ingredients may be obtained as Dub SSIC, Dow 9546 or 9548 Elastomer Blend, or Zano 10 Plus, Allianz OPT or paraben-free Alllianz OPT c5G, Venuceane, Tcote 031, Vital ET, Unilucent PA-13, Revinage, P-50 Liquid, Unipure Red, Yellow and Black, and Vanilla Extract K5035. In alternate embodiments, SolTerra Boost, Zinclear IM 50CCT, and/or Dow 749 Fluid may be optionally used.

In one embodiment, a thickener is provided in a range of about 0.1-10% of the total formulation (e.g., 0.1%, 0.5%, 1%, 2%, 3%, 4%, 5%, 10%, and ranges in between). The thickener can optionally include methycellulose in alternate embodiments.

In several embodiments, the formulation can have an SPF between 5 SPF and 100 SPF. In some embodiments, the topical composition can have an SPF of 15, 20, 25, 30, 35, 40, 45, 50, 60, 70, 80, 90, 100, and ranges in between. Greater SPF values may also be used in some embodiments. A physical sunscreen with an SPF of 50 is provided in several embodiments.

In several embodiments, the formulation comprises a stabilizer, suspending agent and/or thickener. Dimethicone crosspolymer is a silicon derivative that can be used herein as a stabilizing or a suspending agent or a thickener. Types of dimethicone crosspolymers that can be used as a stabilizing agent, suspending agent or a thickener include, but are not limited to, silicone CS-1600, which is a mixture between dimethicone crosspolymer and cyclopentasloxane, dimethicone crosspolymer 3, dimethycone crosspolymer PEG-8, cetyl dimethicone/dimethicone cross polymer, and dimethicone/vinyl dimethicone crosspolymer, and combinations thereof.

Glyceryl isostearate is a type of glyceryl monoester that can be used herein. Glyceryl isostearate can be used as a skin conditioning agent and an emollient. In several embodiments described herein, the topical composition can comprise an emollient. In several embodiments described herein, the topical composition can comprise a skin conditioning agent. In several embodiments described herein, the topical composition can comprise a glyceryl monoester. Glyceryl monoesters that can be used in skin care and treatment can also include, but are not limited to, glyceryl laurate, glyceryl laurate, glyceryl laurate/oleate, glyceryl adipate, glyceryl alginate, glyceryl arachidate, glyceryl behenate, glyceryl caprate, glyceryl caprylate, glyceryl caprylate/caprate, glyceryl citrate/lactate/linoleate/oleate, glyceryl cocoate, glyceryl collagenate, glyceryl erucate, glyceryl hydrogenated rosinate, glyceryl hydrogenated soyate, glyceryl hydroxystearate, glyceryl isopalmitate, glyceryl isostearate, glyceryl isostearate/myristate, glyceryl isostearates, glyceryl lanolate, glyceryl linoleate, glyceryl linolenate, glyceryl montanate, glyceryl myristate, glyceryl isotridecanoate/stearate/adipate, glyceryl oleate, glyceryl oleate/elaidate, glyceryl palmitate, glyceryl palmitate/stearate, glyceryl palmitoleate, gyceryl pentadecanoate, glyceryl polyacrylate, glyceryl rosinate, glyceryl sesquioleate, glyceryl/sorbitol oleate/hydroxystearate, glyceryl stearate/acetate, glyceryl stearate/maleate, glyceryl tallowate, glyceryl thiopropionate, and glyceryl undecylenate.

Polyhydroxystearic acid is a suspending agent and an emulsifier that is used to stabilize products. It can be used herein to suspend SPF protection components in lotions, liquids and gels.

Decamethylcyclopentasiloxane is a cyclopentasiloxane, a silicone fluid that can be used herein. It can work as an emollient for the skin. Trimethylsiloxysilicate can be used for an antifoaming agent, an emollient, and/or for conditioning the skin. In some embodiments, trimethylsiloxysilicate is a cross-linked silicone resin with film-forming attributes. It can hold pigments in place while providing water-resistance in some embodiments. In some formulations herein, it provides a long-lasting effect. In several embodiments, trimethylsiloxysilicate may reduce the number of times the formulation needs to be applied. Trimethylsiloxysilicate is a siloxane polymer. Other examples of siloxane polymers that can be used herein include silica silylate, silica dimethyl silylate, and trifluoropropyldimethyl/trimethylsiloxysicate. In some embodiments, they are insoluble in water and used for film forming, wear and water resistance. In several embodiments described herein, the formulation comprises a siloxane polymer.

Glycerin is also known as glycerol, or glycerine. It is a viscous liquid used in pharmaceutical formulations and cosmetic formulations. Glycerin comprises a glycerol backbone, and is central to all lipids and commonly known as a triglyceride. Several types of triglycerides can be used herein. These can be for example, caprylic/capric triglycerides, triglycerides with C10-C18 fatty acid chains, and triglycerides with C18-C36 fatty acid chains. Fatty acids can include for example, naturally occurring fatty acids which can vary in chain length from 6 to 24 carbon atoms, and can include both saturated and unsaturated fatty acids containing one or more double bonds, and other fatty acids that are known to those skilled in the art. Triglycerides are used herein in some embodiments as an emollient for the skin.

In several embodiments described herein, the topical formulation comprises *bidens pilosa* extract to beneficially affect melanin transport. In other embodiments, this extract can help improve skin radiance and texture by, for example, encouraging cell turnover and may have retinoid-like activity. *Bidens pilosa* extract can be combined with various oils and tocopherol in several embodiments. For example, *Elaeis guineensis* (palm) oil comes from a palm species. This vegetable excipient can be used as a skin conditioning agent and as an emollient. *Gossypium herbaceum* (cotton) seed oil is a vegetable excipient. Cottonseed oil and ingredients made from cottonseed oil can be used herein as excipients with emollient properties. *Linum usitatissimumn* (linseed) seed oil also known as flaxseed oil can be obtained from the dried, ripened seeds of the flax plant and can function as an excipient and/or a skin-conditioning agent herein. Tocopherol is a vitamin E compound, with benefits described herein.

*Bidens pilosa* extract combined with acetyl *rheum rhaponticum* root extract work synergistically in several embodiments to enhance the anti-melanin effects. In some embodiments, the ratio of *bidens pilosa* and a *rheum rhaponticum* extract is 1:1, 1:2, 1:3, 1:4, 1:5, 1:10, 1:25, and ranges in between. In some embodiments, the ratio of the *rheum rhaponticum* extract and *bidens pilosa* is 1:1, 1:2, 1:3, 1:4, 1:5, 1:10, 1:25, and ranges in between. The two agents when combined work synergistically as anti-melanin agents, and further when combined with vitamin E compounds, provide enhanced synergy with the anti-inflammatory effects. Additionally, when combined with a high SPF (such as SPF 30, 50 or more), the formulations' effects on lightening skin are further pronounced. In some embodiments, the ratio of vitamin E compounds (or other anti-inflammatory agents) to the anti-melanin agent(s) is 1:1, 2:1, 3:1, 4:1, 5:1, 10:1, 25:1, and ranges in between.

As described herein, anti-inflammatory agents other than vitamin E compounds can be used in addition to, or in lieu of, vitamin E compounds. Anti-inflammatory agents are used, in some embodiments, to inhibit the inflammatory pathway that can affect melanin. For example, during the inflammatory process in the epidermal layer, inflammatory mediators (such as cytokines, chemokines, prostanoids such as prostaglandins, reactive oxygen species, etc.) may be released. The inflammatory mediators, in turn, may stimulate melanocytes to affect the production, sequestering, and/or processing of melanin in a manner that contributes to hyperpigmentation. An anti-inflammatory agent, as used herein in several embodiments, interrupts (e.g., or otherwise inhibits) this pathway, which in turn helps to reduce hyperpigmentation. In some embodiments, the balancing of inflammation and inflammatory pathways is accomplished.

In several embodiments, the invention comprises or consists essentially of cyclopentasiloxane, isocetyl stearoyl stearate, dimethicone crosspolymer, *thermus thermophillus* ferment, water/aqua/eau, dimethicone/vinyl dimethicone crosspolymer, disodium lauriminodipropionate tocopheryl phosphates, panthenyl triacetate, acetyl *rheum rhaponticum* root extract, dimethiconol, *citrus paradisi* seed extract, glycerin, dimethicone, *fusanus spicatus* wood oil, *vanilla planifolia* fruit extract, caprylic/capric triglyceride, *elaeis guineensis* (palm) oil, *bidens pilosa* extract, *gossypium herbaceum* (cotton) seed oil, *linum usitatissimum* (linseed) seed oil, tocopherol, a glycol (such as propylene or pentylene glycol), acrylates/C12-22 alkyl methacrylate copolymer, ascorbic acid, phenoxyethanol, benzoic acid, dehydroacetic acid, potassium sorbate, triethoxycaprylylsilane, farnesol, and iron oxides (e.g., CI 77491, CI 77492, CI 77499).

In several embodiments, the invention comprises or consists essentially of cyclopentasiloxane, isocetyl stearoyl stearate, dimethicone crosspolymer, *thermus thermophillus* ferment, water/aqua/eau, dimethicone/vinyl dimethicone crosspolymer, disodium lauriminodipropionate tocopheryl phosphates, panthenyl triacetate, acetyl *rheum rhaponticum* root extract, dimethiconol, *citrus paradisi* seed extract, glycerin, dimethicone, *fusanus spicatus* wood oil, *vanilla planifolia* fruit extract, caprylic/capric triglyceride, *elaeis guineensis* (palm) oil, *bidens pilosa* extract, *gossypium herbaceum* (cotton) seed oil, *linum usitatissimum* (linseed) seed oil, tocopherol, a glycol (such as propylene or pentylene glycol), acrylates/C12-22 alkyl methacrylate copolymer, ascorbic acid, phenoxyethanol, benzoic acid, dehydroacetic acid, potassium sorbate, triethoxycaprylylsilane, farnesol, titanium dioxide (CI 77891), zinc oxide (CI 77947), iron oxides (e.g., CI 77491, CI 77492, CI 77499).

In several embodiments, the invention comprises or consists essentially of titanium dioxide, zinc oxide, cyclopentasiloxane, water (aqua), dimethicone crosspolymer, caprylic/capric triglycerides, trimethylsiloxysilicate, *thermus thermophillus* ferment, dimethicone/vinyl dimethicone crosspolymer, methycellulose, panthenyl triacetate, acetyl *rheum rhaponticum* root extract, disodium lauriminodipropionate tocopheryl phosphates, grapefruit seed extract, *bidens pilosa* extract, *fusanus spicata* wood oil, *elaeis guineensis* (palm) oil, tocopherol, *gossypium herbaceum* (cotton) seed oil, *linum usitatissimum* (linseed) seed oil, glycerin, glyceryl isostearate, dimethiconol, triethoxycaprylylsilane, ascorbic acid, *vanilla planifolia* fruit extract, dimethicone, polyhydroxy stearic acid, phenoxyethanol, potassium sorbate, dehydroacetic acid, benzoic acid, and iron oxides (e.g., CI 77491, CI 77492, CI 77499).

The topical formulations described herein may be used as a primer. In addition, according to several embodiments, the formulations may be foundation, blush, lip color, eye color, lotions, creams, serums, gels, cleansing formulations, eye creams, sunscreens, bronzers, powders, nail care, hair care, and other cosmetics and skin care products.

According to several embodiments, the ingredients may be delivered in a single formulation or separately. For example, the anti-melanin agent and the anti-inflammatory agent and sunscreen can be in a single formulation. Alternatively, the ingredients or groups of ingredients may be provided in separate compositions. For example, the anti-melanin agent(s) and the anti-inflammatory agent(s) may be in one formulation and the sunscreen in another. The topical formulations are, according to several embodiments, applied once a day, twice a day, or every other day. Greater frequencies may also be used. Lesser frequencies may also be used, for example in maintenance phase after the desired effects have been achieved. Multi-chamber dispensers can be used in some embodiments. In several embodiments, a kit comprising a formulation and one or more skin care or cosmetic products is provided. In one embodiment, the kit comprises the anti-melanin and anti-inflammatory agents in one unit and the sunscreen separately. In one embodiment, the kit comprises the anti-melanin and anti-inflammatory agents in one formulation and, optionally, a separate keratolytic. Applicators (brushes, sticks, sponges, etc.) may be provided to apply the formulations described herein, and may also be included in a kit. The kit can comprise one or more of the formulations described herein in varying strengths (e.g., of the active ingredients). The kit can comprise one or more of the formulations described herein as well as an addition sunscreen and/or exfoliant. In some embodiments, the formulations described herein can be applied by transdermal patch.

In several embodiments, hyperpigmentation is reduced by 10-100% after use. For example, significant lightening effects and improvements in pore size, fine lines, overall appearance, radiance, skin smoothness, and/or skin tone (evenness) are visible in several embodiments after 4 weeks, 8 weeks and 12 weeks. Certain improvements in skin may be visible or felt upon use or within days of use. Although specific regions of hyperpigmentation are treated according to several embodiments, an overall lightening or brightening effect can also be achieved on skin that has no identifiable regions of hyperpigmentation.

Several embodiments of the formulations are particularly advantageous because they provide coverage (e.g., color, camouflage) in a formulation that goes on smoothly and is not chalky or sticky. This is helpful to cover areas of hyperpigmentation while the formulation is simultaneously working to reduce said hyperpigmentation. This is also helpful to minimize the number of products a user applies to his/her face (or body) because it reduces the need for a separate foundation.

Several embodiments of the formulations are water resistant. In one embodiment, the formulation is water resistant, e.g., with respect to SPF, for up to 30, 40, 60 and 120 minutes. Long-wear formulations are provided in several embodiments.

The formulations, according to several embodiments, are especially effective because they offer a multi-modal approach to reduction of hyperpigmentation. The combination of the anti-melanin agent with the anti-inflammatory and sunscreen provides a multi-modal approach that addresses discoloration via multiple pathways and results in the creation of a unique and effective formulation. In several embodiments, the anti-inflammatory agents, by acting through a pathway that involves inflammation's role in hyperpigmentation, are particularly effective when combined with the anti-melanin agents.

In some embodiments, one or more keratolytic agents may be optionally included. For example, one embodiment comprises or consists essentially of one or more keratolytic agents, one or more anti-melanin agents (such as tyrosine inhibitors), one or more anti-inflammatory agents, and one or more sun protection agents. The keratolytic agent(s), anti-melanin agent(s) (such as tyrosine inhibitors), and anti-inflammatory agent(s) (such as vitamin E compounds) work synergistically together in many embodiments to counter undesired pigmentation. The keratolytic agents used herein can, in one embodiment, break down the keratinized outer layer of the epidermis. Keratolytic agents may help remove or soften older, damaged surface tissue (e.g., keratin) and promote the generation of new skin cells. In several embodiments, keratolytic agents are retinoid-like compounds (such as from a vegetable or botanical source), improve skin radiance and texture, produce a lightening effect, reduce melanin, and or restore firmness. Keratolytic agents used in the formulations described herein include but are not limited to one or more of the following: extracts from the aster family of plants (such as asteraceae, *bidens pilosa*), salicylic acid, alpha hydroxy acid, beta hydroxy acid, sulfur, azelaic acid, glycolic acid, urea, lactic acid, resorcinol, allantoin, and fruit acids. In some embodiments, the keratolytic agent includes *bidens pilosa* extract, and one or all of palm oil, cottonseed oil, linseed oil and tocopherol. In some embodiments, exfoliants are used in addition to or in lieu of keratolytic agents. Exfoliants can be chemical or mechanical. The keratolytic agents are provided, in several embodiments, in a range of about 0.005% to about 10% (e.g., 0.005%, 0.05%, 0.1%, 0.5%, 1%, 5%, 10%, and ranges in between) % m/m, % m/v, or % v/v in the formulation. In some embodiments, the ratio of the keratolytic and the anti-melanin agent is 1:1, 1:2, 1:3, 1:4, 1:5, 1:10, 1:25, and ranges in between. In some embodiments, the ratio of the anti-melanin agent and the keratolytic is 1:1, 1:2, 1:3, 1:4, 1:5, 1:10, 1:25, and ranges in between. Although *bidens pilosa* may have keratolytic properties in some aspects, several embodiments include *bidens pilosa* for its anti-melanin properties rather than its keratolytic properties.

Soothing Redness Corrector Formulations

Despite the large number of skin care formulations on the market, there remains a need for a formulation that simultaneously reduces skin redness and skin irritation in a multi-modal manner, offers significant UV protection (such as physical UVA and UVB sun protection), and provides color correction, all in a non-irritating formulation that goes on smoothly. Because redness can correlate with inflammation and sensitivity, there is a particular need for a formulation that is both efficacious and suitable for sensitive skin, and additionally incorporates a broad-spectrum sunscreen, without being irritating or chalky.

Several embodiments of the present invention meet the needs recited above. In several embodiments, the invention comprises a unique topical formulation with an SPF of at least 30 (e.g., 50) for neutralizing redness and soothing sensitive skin comprising niacinamide, bisabolol, tocopheryl phosphates (a vitamin E compound), *Crithmum maritimum* extract, *Magnolia officinalis* bark extract, and *Zingiber officinale* (ginger) root extract, magnesium carboxymethyl beta-glucan, and jojoba esters, as well as other ingredients.

In many embodiments, the reduction of inflammation through the inclusion of an anti-inflammatory agent synergistically works with the other ingredients to counter skin redness/irritation via multiple pathways to inflammation, promote skin repair and improve overall skin health. The inflammation and irritation that is ameliorated by several embodiments herein may have been caused by, for example, an immune response (e.g. allergy), genetics, the aging process, or environmental causes (such as UV exposure).

Several embodiments disclosed herein provide for comprehensive skin care formulations that target one or more inflammatory mediators, thereby serving as anti-redness and anti-irritants and providing soothing, healing, or otherwise soothing effects for sensitive, reddened, or otherwise irritated skin. In several embodiments, the formulations improve the barrier function of the skin through the protection and/or enhancement of epidermal lipids, boosts cellular respiration and restores the water balance. Several embodiments improve the radiance of damaged skin, and in some embodiments also improve radiance and appearance of normal skin. In several embodiments, the formulations provided rebalance the skin's immune system, which leads to soothing of irritated, itching or otherwise sensitive skin.

In some embodiments, a multi-modal approach effectively soothes the skin. In one embodiment, inflammation is reduced by at least 10-90% post treatment with a formulation as described herein used consistently after 7, 14, 21, 30, 60 or 90 days. In one embodiment, cytokines are reduced by at least 10-90% post treatment with the formulation used consistently after 7, 14, 21, 30, 60 or 90 days. In one embodiment, skin irritation is reduced by at least 10-90% post treatment with the formulation used consistently after 7, 14, 21, 30, 60 or 90 days. In one embodiment, skin redness is reduced after 1-3 uses of the formulation by at least 10-75%. Wound healing, such as micro-wounds and abrasions, is also improved in one embodiment by at least 10-90% post treatment with the formulation used consistently after 7, 14, 21, 30, 60 or 90 days.

In some embodiments, the formulations provided herein are concentrated and provided in a mask form to be left on the skin for at least 5, 15, 30, or 60 minutes (or as an overnight night repair mask) for accelerated results. Optionally, the mask may include ingredients such as camphor, almond extract, honey, kaolin, basil, turmeric, and/or kelp. The non-mask formulations may also include camphor, almond extract, honey, kaolin, basil, turmeric, and/or kelp. Gentle cleansers may also include many of the ingredients of the formulations described herein and may additionally include witch hazel or other toners (for toner-type cleansers) or foaming ingredients (for washes and foaming cleansers). Concentrated spot treatments are provided in some embodiments. In one embodiment, the amounts of the ingredients are concentrated by 10% or more (as compared to the non-masks) and provided as a mask.

In some embodiments, visible reductions in the appearance of redness and inflammation may be observed within minutes of use of a formulation as described herein, due to, for example, the color correction pigments and/or the anti-inflammatory activity of the ingredients. A soothing or cooling sensation may be experienced by the user upon application to the skin.

In some embodiments, the formulations for treating skin redness and/or irritation are used during or after a dermatological procedure (including but not limited to brow lifts, blepharoplasty, botulin and other neurotoxins, facials, fillers, dermabrasion, microdermabrasion, micro-needling, peels, exfoliations, suctioning, fluid delivery, acid treatments, massage, extractions, energy-based and other treatments, such as lasers, thermal, radiofrequency, light (e.g., photofacials/IPL), etc.).

Several embodiments disclosed herein provide for a formulation for treating skin redness and/or irritation, the formulation including a niacinamide, a *Zingiber officinale* extract, bisabolol (natural or synthetic) or an asteraceae extract, a *Crithmum maritimum* extract, a *Magnolia officinalis* extract, and a Vitamin E compound. In several embodiments, the formulation further comprises at least one sunscreen agent. In several embodiments, zinc oxide is used as a sunscreen. In some embodiments, titanium dioxide is used. In still additional embodiments, a combination of zinc oxide and titanium dioxide is used. In several embodiments, effective (e.g., therapeutic) amounts of ingredients are included in the formulation. An effective (e.g., therapeutic) amount, in one embodiment, may be that which reduces redness and/or irritation after at least 1-18 months (e.g., 4-12 weeks) of twice daily use.

In several embodiments, there is provided a high SPF (sun protection factor) formulation for treating skin redness and irritation, the formulation comprising (i) a first skin care agent (e.g., *Zingiber officinale* extract) (ii) a second skin care agent (e.g., bisabolol (natural or synthetic) or an asteraceae extract) (iii) a third skin care agent (e.g., *Crithmum maritimum* extract) (iv) a fourth skin care agent, wherein the fourth skin care agent additionally functions as an antimicrobial (e.g., *Magnolia officinalis* extract) (v) an anti-inflammatory agent (e.g., vitamin E based compound), (vi) niacinamide, and (vii) a sun protection agent comprising zinc oxide and/or titanium dioxide, wherein the formulation is a topical formulation suitable for topical delivery. Effective amounts of these ingredients are provided in several embodiments.

In several embodiments, there is also provided a topical formulation for treating skin redness and irritation comprising two or more of niacinamide, a *Zingiber officinale* extract, bisabolol (natural or synthetic) or an asteraceae extract, a *Crithmum maritimum* extract, a *Magnolia officinalis* extract, a Vitamin E compound, a zinc oxide; and a titanium dioxide. In one embodiment, the two or more ingredients interact in a multi-modal and/or synergistic manner. Effective amounts of these ingredients are provided in several embodiments.

In several embodiments, niacinamide (or a derivative thereof) is used to achieve one or more of the following benefits: reduced skin redness, reduced irritation, reduced blotchiness, reduced wrinkle appearance, increased elasticity, ceramide production, and hydration, and additionally in some embodiments, achieves a synergistic effect when combined with at least one of the following ingredients: bisabolol, a *Zingiber officinale* extract, a *Crithmum maritimum* extract, a *Magnolia officinalis* extract and sunscreen. The synergism achieves a beneficial result that is more efficacious than the additive effects of the ingredients, according to some embodiments.

In several embodiments, such formulations provide a sun protection factor of SPF 30 or more (e.g., 30, 40, 50, 70, 90, 100 SPF or more). In several embodiments, the formulation is provided as a topical formulation. In several embodiments, the formulation is provided in the form of a liquid, cream, serum, or gel. Other embodiments of the formulation are provided as a powder, powder spray, aerosol, roll-on, stick, or the like. In several embodiments, the *Zingiber officinale* extract is a root or leaf extract. In several embodiments, the *Magnolia officinalis* extract is a root, leaf or bark extract.

In several embodiments, the formulation further comprises caprylic/capric triglycerides. In several embodiments, the caprylic/capric triglycerides act as skin conditioners and/or occlusive agents, the latter serving, in several embodiments, to increase the hydration of the skin (e.g., by preventing loss of moisture through the skin), thereby reducing the tendency of dry skin to become irritated or itchy. In several embodiments, the formulation further comprises a beta-glucan compound. In one embodiment, the beta-glucan comprises magnesium carboxymethyl beta-glucan. In several embodiments, the beta-glucan is yeast derived, for example baker's yeast. In several embodiments, the beta-glucan serves as a skin conditioner and/or serves to protect skin cells against depletion of endogenous antioxidant compounds (e.g., upon exposure to UV radiation). In several embodiments, the beta-glucan aids in the renewal rate of certain types of skin cells, such as cells of the stratum corneum layer.

In several embodiments, the formulation further comprises one or more siloxane. In several embodiments, the siloxane comprises cyclopentasiloxane. Other siloxanes are used, in several embodiments, depending on the embodiment, for example those with 4, 5, or 6 siloxane groups. In several embodiments, the siloxane (e.g., cyclopentasiloxane) is provided in a range of 30-60% as % m/m of the formulation (e.g., 30%, 40%, 50%, 60%, and ranges in between). In other embodiments, these ingredients are provided as % w/w, % m/v, % v/v, % m/w, or % w/v.

In several embodiments, the formulation comprises an extract derived from a member of the asteraceae family. For example, in several embodiments the asteraceae extract is derived from the root, leaf, flower or other part of the chamomile flower. In several embodiments, the asteraceae extract comprises bisabolol. In several embodiments, a synthetic bisabolol, or synthetic version of an asteraceae extract is used. In several embodiments, the asteraceae extract provides one or more of anti-irritant, anti-inflammatory and anti-microbial properties. Anti-microbial agents are used, in some embodiments, with agents that encourage the maintenance of a healthy skin biome (probiotics, etc.). Bisabolol may be obtained from *Matricaria* and *Vanillosmopsis* extracts (such as *Matricaria chamomilla, Matricaria recutita, Vanillosmopsis erythropappa*) or other sources.

In several embodiments of the formulation the *Zingiber officinale* extract (e.g., root or other extract) is provided in a range of 0.005-5% (e.g., 0.005%, 0.01%, 0.05%, 0.1%, 1%, 2.5%, 50%, etc.), and the bisabolol (natural or synthetic) or asteraceae extract is provided in a range of 0.05-5% (e.g., 0.05%, 0.1%, 1%, 2.5%, 50%, etc.). The percentages are provided as % m/m in some embodiments. In other embodiments, these ingredients are provided as % w/w, % m/v, % v/v, % m/w, or % w/v.

In several embodiments of the formulation, niacinamide is provided in a range of 0.5-5% (e.g., 1-3%, 2%, 3%, etc.), *Zingiber officinale* extract is provided in a range of 0.005-5% (e.g., 0.002%, 0.004%, 0.01%, 0.1% etc.), bisabolol (natural or synthetic) or asteraceae extract is provided in a range of 0.05-5% (e.g., 0.05%, 0.1%, 1%, 2.5%, 50%, etc.), *Crithmum maritimum* extract is provided in a range of 0.02-5% (e.g., 0.02%, 0.05%, 0.1%, 1%, 2.5%, 50%, etc.), *Magnolia officinalis* extract (e.g., bark extract) is provided in a range of 0.001-5% (e.g., 0.001%, 0.005%, 0.01%, 0.05%, 0.1%, 1%, 2.5%, 50%, etc.), and a Vitamin E compound is provided in a range of 0.05-5% (e.g., 0.05%, 0.1%, 1%, 2.5%, 50%, etc. The percentages are provided as % m/m in some embodiments. In other embodiments, these ingredients are provided as % w/w, % m/v, % v/v, % m/w, or % w/v. In several embodiments, the Vitamin E compound comprises tocopheryl, tocopheryl phosphate or other derivative thereof. In several embodiments, the vitamin E compound comprises a disodium lauriminodipropionate tocopheryl phosphate.

In several embodiments, the formulation is paraben-free and is configured for use on the face. In several embodiments, the formulation is a free from animal products (e.g., the components of the formulation are plant-based or synthetic). In several embodiments, the formulations provided for herein are suitable for daily topical application, and rated at Protection Grade of Ultraviolet A (PA) of 12-14, 14-16, 16-18 or greater (or any grade in between those listed) in a Persistent Pigment Darkening (PPD) test.

In several embodiments, there is also provided a use of a formulation disclosed herein for the treatment or prevention of red, irritated or inflamed skin. In several embodiments, the use of the formulations disclosed herein quickly neutralizes or reduces or eliminates the appearance of redness on skin. In several embodiments, use of the formulations helps to soothe and calm sensitive skin, while, in several embodiments, providing protection from sun exposure. In several embodiments, the formulation provides ongoing relief from sensitivity and/or the appearance of redness.

Also provided for herein are methods for treating red, sensitive, and/or irritated skin, the methods comprising identifying at least one region of skin tissue exhibiting redness, sensitivity or irritation, and applying, or instructing application of, a topical formulation to the skin region, wherein the formulation conditions the red or irritated skin, reduces inflammatory mediators in the region of skin tissue, and provides protection from ultraviolet rays, wherein the formulation comprises niacinamide, a *Zingiber officinale* extract, bisabolol (natural or synthetic) or an Asteraceae extract, a *Crithmum maritimum* extract, a *Magnolia offinicalis* extract, a Vitamin E compound, a zinc oxide; and a titanium dioxide.

In several embodiments, the formulations provided for herein function to alleviate one or more pathways that can contribute to skin redness and/or irritation. For example, mechanical factors may cause skin redness and/or irritation in some embodiments. Additionally, physical and/or chemical factors may also play a role in development of skin redness and/or irritation, either alone or in combination with mechanical factors. Non-limiting examples of mechanical factors that can cause, contribute to or are associated with skin redness and/or irritation include mechanical hair removal, such as shaving or waxing, scrapes, abrasions (e.g., first, second or third degree), heat or drying effects from external sources, such as a hair dryer, or other mechanical means that create friction against the skin and can damage or injure one or more skin layers. In some embodiments, physical factors work in conjunction with mechanical factors to lead to skin redness and/or irritation. Physical factors include, but are not limited to, UV exposure (e.g., sunlight), varied temperatures—whether hot or cold, either of which can cause an imbalance in skin health, other environmental factors such as humidity, and the like. For example, a cold environment can cause drying of skin, in part because of lower humidity, with the drying of the skin leading to cracking or other skin damage/loss of hydration, which can lead to skin irritation or redness. Similarly, elevated temperatures or high humidity can cause excessive perspiration or greater than normal moisture on skin surfaces, which can then lead to development of frication and/or skin abrasions, which as discussed above can lead to skin damage. Chemical factors, which may work in combination with physical and/or mechanical factors, can cause also skin irritation or redness. Chemical factors include, but are not limited to, certain sunscreens or other topical compositions (e.g., lotions, facial masks etc.,), chemical hair removal agents, retinol (e.g., retinoid skin creams), exposure to preservatives (e.g., those in certain topical formulations).

In several embodiments, mechanical, physical, or chemical factors (or combinations of any or all of such factors) that can affect skin negatively are treated by the formulations described herein; for example one or more of these factors can initiate or otherwise promote skin redness, irritation or damage through damage or injury to the outer layers of skin, which normally function as a protective barrier. In some embodiments, these factors can cause a loss of natural or endogenous moisturizing factors, which can lead to dryness, loss of skin hydration and susceptibility to other pro-damaging factors or environments. Loss of lipids (e.g., epidermal lipids in the stratum corneum) can further degrade the barrier function of the skin, rendering it more susceptible to other factors and possibly to infectious agents. Pro-damaging factors can also lead to loss of, degradation of, or reduced production of certain skin proteins. Various proteins serve to maintain the working structure of skin cells, maintain a tight and intact external skin layer, and generally promote and maintain the barrier function of skin.

At least one result of the damages to the skin or reduction in barrier function is the subsequent cascade of biochemical events that occur in deeper layers of the skin, such as the epidermis. In the epidermal layer, a series of proinflammatory reactions can occur as a result of mechanical, chemical and/or physical events. For example, various proinflammatory cytokines can be released (II-1alpha, leukotriene B4, tumor necrosis factor alpha, prostaglandin E2, etc.). In several embodiments, there are multiple cascades or layers of proinflammatory cytokines. In some embodiments, one or more of the proinflammatory cytokines are released from, for example, keratinocytes and/or mast cells. These proinflammatory cytokines can have wide ranging effects, from local infiltration of immune cells, to activator of downstream receptors, such as heat receptors (which later impact neural sensory pathways to further exacerbate skin irritation. Further, mast cells can also release mediators of itching sensations (e.g., histamine). These various proinflammatory cytokines can activate cognate receptors and induce a change in neural signals that lead to an increased sensation of itching, burning, skin tightness, heat, etc. Not only does the activation of these pathways lead to the increased sensations of irritation, the increased sensations can lead to an individual exacerbating the problems (e.g., by itching the skin, further damaging the surface and generating more inflammatory mediator release), as well as additional reddening of the skin.

Furthermore, there can result, in several embodiments, more long term changes to the cells making up the various skin layers. For example, there can be alterations in proliferation and/or differentiation of cells in the skin. In one embodiment, keratinocytes, which serve as barrier cells, can overproliferate which can lead to a coordinate excess of proinflammatory cytokine production and/or skin thickening. Likewise, changes in keratinocyte differentiation can be altered, thereby altering the balance between the various types of cells in the skin. These longer-term changes can result in a feed forward effect that leads to further skin susceptibility to the various factors that led to initial injury (e.g., mechanical, physical, chemical). As a result, the skin's natural barrier function can continue to degrade, which leads to dry, damaged, and sensitive skin—such characteristics being associated with increased chances for additional skin damage and irritation. Thus, mechanical, physical and/or chemical factors can create a cycle or loop of skin irritation and redness.

In several embodiments, the formulations described herein address (e.g., limit the effects of) one or more of these causes and/or symptoms of damaged, irritated, or reddened skin. In several embodiments, the formulations described herein reduce the impact of mechanical factors on the skin and its barrier function. In several embodiments, the formulations provided for herein reduce the impact of chemical factors on the skin and its barrier function. In several embodiments, the formulations described herein reduce the impact of physical factors on the skin and its barrier function. In several embodiments, the formulations described herein limit release and/or effect of proinflammatory cytokines and/or other inflammatory mediators. In several embodiments, the formulations provided for herein limit the longer-term changes that could negatively impact skin, thereby limiting or reducing the feed-forward effect discussed above. In one embodiment, the formulations described herein maintain or enhances lipid production in the skin, for example, by stimulation of synthesis of certain ceramides, which are major components of the stratum corneum. In several embodiments, production of ceramides such ceramide III or VI, and/or enzymes that play a role in ceramide formation (e.g., beta-glucocerebrosidase) is elevated through use of the formulations described herein, which can enhance barrier function (and also moisture retention). In several embodiments, production or maintenance of other structural components of the skin, such as filaggrin (monomers that are incorporated into skin lipids, thereby enhancing skin barrier function) is increased through use of the formulations described herein, which enhances the ability of the skin to resist negative impacts of mechanical, physical and/or chemical factors (and thus become less susceptible to irritants).

In still additional embodiments, the formulations described herein enhance one or more of skin cell regulation and overall skin protection. Cellular regulation of skin cells can be positively impacted by the formulations provided for, for example, by promoting proliferation of certain cells, such as epidermal basal cells. Also enhanced in several embodiments is cellular respiration. In conjunction, these effects result in a larger overall population of healthy skin cells, with each cell, or the majority of cells, undergoing greater regulation of cellular respiration to avoid or eliminate, for example, free radical production or other factors (e.g., production of proinflammatory cytokines) that could compromise skin function or integrity. Skin protective effects are also achieved through the use of formulations disclosed herein. For example, in several embodiments, the formulations regulate (e.g., reduce) proinflammatory mediators. Additionally, cellular stressors (e.g., free radicals resulting from oxidative/metabolic stress) are regulated (e.g., reduced to a normal, healthy level). In several embodiments, the formulations also provide an increased barrier function that allows the cells of the skin to become properly hydrated (thereby increasing the water reservoir of the skin) and also preventing or reducing loss of water through the skin, especially damaged skin.

In several embodiments, the topical formulation is a liquid, cream, serum, or gel. Depending on the embodiment, at least one of the *zingiber officinale*, bisabolol (natural or synthetic) or an asteraceae extract, *Crithmum maritimum*, and *Magnolia officinalis* extracts are root extracts. In several embodiments, the topical formulation decreases production of inflammatory mediators, improves the barrier function of the skin, leading to improved hydration and antioxidant production, and/or conditions the skin while providing protection from UV exposure.

The use of agents, ingredients and compounds may be used interchangeably herein. In several embodiments, reference to the term "based" includes the recited agent, ingredient or compounds. For example, a bisabolol-based compound includes panthenol itself. As used herein, the terms composition and formulation can be used interchangeably. As used herein, the terms "skin care formulation(s)" and "cosmetic formulation(s)" can be used interchangeably. Where percentages are provided for agents, ingredients and compounds, they can be % m/m, % m/w, % w/w, % m/v, % v/v and variations thereof with respect to the formulation as a whole, unless otherwise indicated.

The agents, ingredients and compounds described herein may be modified natural substances (e.g., isolates, extracts, purified, processed, chemically modified, etc.) or synthetic substances. Methods of using unique combinations of natural substances are also provided.

In several embodiments, the invention comprises a method of treating skin using any one of the formulations described above or below. The use of any of the formulations described herein for treating skin (e.g., reducing skin irritation or redness) and/or improving skin appearance is provided in several embodiments. Several embodiments also include instructing the method or use of the formulation (e.g., via instructions for use).

As described above, several embodiments of the present invention (e.g., calming formulations) relate to unique skin care formulations for treating, protecting, and/or repairing skin. The formulations described herein can be beneficial for both healthy and damaged skin, for example skin that is irritated through aging, sun exposure, or other environmental stress. In several embodiments, use of the formulations described herein provides one or more of the following advantages: (i) reduction in the appearance of redness and/or blotchiness, (ii) reduction in skin irritation, aggravation, and/or discomfort, etc., (iii) skin looks and feels smoother; (iv) increased firmness, (v) increased hydration, (vi) improved skin tone and texture (e.g., increased evenness), (vii) clearer complexion, (viii) improved radiance, (ix) fine lines, pores, and wrinkles appear less visible, (x) improved overall appearance of skin, (xi) reinforcement of the skin's natural defenses, (xii) improved epidermal structural integrity (e.g., improvement of the skin's barrier function), (xiii) reduction or prevention of inflammation, (xiv) rebalancing of the skin's immune system, (xv) soothing of irritated skin, and (xvi) calming of sensitive and/or itchy skin. Advantageously, in several embodiments, these improvements are obtained with formulations that are gentle and non-irritating, with no or little erythema, edema, dryness, peeling, itching, stinging, tingling, or burning sensation. Because undesired effects are nominal or nonexistent, the formulation fosters regular use by a subject (even one with sensitive skin), which enables longer term improvements in skin characteristics.

The formulations described herein can provide both short-term and long-term benefits according to several embodiments. Beneficial effects from use of the formulations described herein occur upon use, within hours of use, within 1-2 days, 3-4 days, about 7 days, about 14 days, or within about 3 weeks. In several embodiments, the skin appears improved after application of the formulation and benefits continue over about 2-6 weeks, about 6-12 weeks, about 12-24 weeks, or about 24-52 weeks of use. In several embodiments, long lasting effects on the skin are achieved in less than 3 months.

Several embodiments of the invention comprise a formulation for soothing irritated skin while also reinforcing the skin's natural defenses. In some embodiments, the formulation optionally includes ingredients that provide protection against UV damage. In some embodiments, the formulation is in a liquid, gel or solid (e.g., powder) form. The formulations described herein can be applied prior to or after foundation or other make-up. In some embodiments, the formulation is colorless; however, in other embodiments, the formulation contains sufficient color to serve as foundation and/or color corrector (e.g., with green undertones to balance redness). In some embodiments, the pH of the formulations is slightly basic, slightly acidic or neutral. In some embodiments, a pH of 3-5, 4-6, 5-7, 6-8, or ranges in between, are provided. Lower or higher pH values may also be used.

The formulations described herein have one or more of the following uses: primer, moisturizer, skin protectant, sunscreen, setting mist, and color (cover-up, coverage, or foundation). The unique aspects of many of the formulations described herein provide a multi-functional product that blends skin care (e.g., skin repair) and sun care, and offers a high SPF primer, color coverage, skin nourishment, antioxidants and an anti-irritant/anti-inflammatory effect (e.g., through a reduction of inflammatory mediators, increasing cellular respiration, restoration of the skin's water balance).

According to several embodiments, the formulations described herein can be applied by hand, by sponge, by spraying, by applicator, by dropper, by brush, or through use of a composition-impregnated wipe or tissue. In some embodiments, the formulations described herein can optionally be applied by transdermal patch. In some embodiments, the formulations are absorbent (e.g., readily absorbable) such that no separate means are needed to enhance absorption. However, in some embodiments, one or more of low frequency ultrasound, massage, application of an electrical field, mechanical manipulation or vibration may be used to facilitate absorption. In some embodiments, the formulation is useful post-surgery or dermatological treatment, where, for example, skin irritation or damage may be an issue. Several topical formulations herein described can penetrate top layers of the skin. Further, some of the formulations described herein may be suitable for use for application under one or more skin layers (e.g., as an injectable or subcutaneous implant).

The invention, according to several embodiments, comprises a topical formulation (such as a liquid formulation with anti-irritant effects) for treating skin that includes extracts of ginger and bisabolol (natural or synthetic) or an asteraceae extract. In one embodiment, the ginger comprises *Zingiber officinale* extracted from the leaf, root, flower or other part of the plant. In several embodiments, the bisabolol (natural or synthetic) or asteraceae extract comprises a sesquiterpene alcohol, such as a monocyclic sesquiterpene alcohol. In several embodiments, bisabolol (also known as levomenol) is used in a synthetic format. In several embodiments, the asteraceae extract is derived from the chamomile leaf, root, flower or other part of the plant. In one embodiment, the bisabolol is provided as an essential oil. In one embodiment, the bisabolol is optionally synthetic. In some such embodiments, synthetic bisabolol may comprise a racemic mixture of α-(−)-bisabolol and α-(+)-bisabolol. *Zingiber officinale* and bisabolol (natural or synthetic) are unrelated compounds that Applicant believes have unexpected synergistic effects in combination to reduce skin irritation, reduce skin redness, or otherwise treat skin. In several embodiments, these compounds synergistically act to reduce one or more inflammatory mediators, such as interleukins and prostaglandins. In one embodiment, these compounds reduce production of, inhibit the activity or, or otherwise diminish the effects of one or more of interleukin 1 alpha, tumor necrosis factor (e.g., TNF alpha), cyclooxygenase (e.g., COX-2) or prostaglandin E2.

In several embodiments, topical formulations provided for herein additionally comprise an extract from the *magnolia* plant. In some embodiments, the *magnolia* extract comprises an extract that is extracted from the leaf, root, flower or other part of the plant. In one embodiment, the *magnolia* extract is extracted from the bark of the plant. In several embodiments, the extract comprises one or more anti-inflammatory substances. For example, the extract comprises, in some embodiments magnolol and/or honokiol. These substances act synergistically to inhibit activation of inflammatory mediators and mediators of skin aging. For example, in several embodiments, the activity of NF-KB is inhibited. Moreover, in several embodiments, the *magnolia* extract acts to protect skin against chronic inflammation, neutralize internal aging factors and to reduce skin redness. In some embodiments, the *magnolia* extract is coupled with one or more triglycerides, such as those derived from coconut oil. In one embodiment, the triglycerides comprise caprylic and capric fatty acids of coconut oil, rather than a complete spectrum of all the fatty acids of coconut oil. In several embodiments, the caprylic and capric fatty acids act synergistically with the *magnolia* extract (or with other ingredients of the composition) to provide anti-inflammatory, anti-irritating, anti-redness effects and/or any of the other positive skin effects disclosed herein.

In several embodiments, the formulations provided herein further comprise one or more *Crithmum* plant extracts. In several embodiments, the extract is extracted from the leaf, root, flower or other part of the plant. In some embodiments, the extract is from *Crithmum maritimum* (e.g., sea fennel or rock samphire). In some embodiments, the plant extract is coupled with one or more triglycerides, such as those derived from coconut oil. As discussed above, in one embodiment, the triglycerides comprise caprylic and capric fatty acids of coconut oil, rather than a complete spectrum of all the fatty acids of coconut oil. In several embodiments, the caprylic and capric fatty acids act synergistically with the plant extract (or with other ingredients of the composition) to provide anti-inflammatory, anti-irritating, anti-redness effects and/or any of the other positive skin effects disclosed herein. For example, in some embodiments, the plant extract and/or caprylic/capric fatty acids maintain or protect the lipids normally present in the epidermis, boost cellular respiration and/or aids in restoration of skin hydration and water balance.

In several embodiments, the formulations provided herein further include a biologically active polysaccharide. In some embodiments, the polysaccharide is a beta glucan. In one embodiment the beta-glucan is a derivative of a yeast beat glucan, for example baker's yeast. In several embodiments, the beta-glucan acts synergistically with one or more other ingredients of the composition to provide anti-inflammatory, anti-irritating, anti-redness effects and/or any of the other positive effects disclosed herein, such as improved wound healing and/or fighting infections. Additionally, in several embodiments, the beta-glucan aids in soothing irritated skin, calming sensitive and itching skin, and generally aids in alleviating skin discomfort.

In some embodiments, the niacinamide, *Zingiber officinale* extract, bisabolol (natural or synthetic) or asteraceae extract, *magnolia* plant extract, marine plant extract/caprylic/capric fatty acids, and biologically active polysaccharide are each provided in the range of about 0.0005-10% and the vitamin-containing compound (or compounds) is provided in the range of about 0.05-10% (respectively, in those embodiments wherein multiple vitamin containing compounds are included). Sunscreen may be provided in the range of about 1-45%. Sunscreen provides an additional benefit by shielding the skin and preventing, minimize or otherwise reducing the skin's exposure to UV, which can reduce environmental damage to the skin, thus facilitating the therapeutic benefits of the formulation. Further, sunscreen reduces the incidence of future inflammation and skin damage. To Applicant's knowledge, several combinations of ingredients disclosed herein represent unique formulations that are not naturally occurring (e.g., not found in nature in such combination). Moreover, in several embodiments, the individual ingredients are modified so as to be structurally and/or functionally different than the naturally-occurring species, thereby resulting in markedly unique effects.

In addition, in some embodiments, at least one of the following ingredients is included: a skin conditioning agent, a solvent, a silicone, an emollient, a preservative, a thickener, an antioxidant, an anti-inflammatory agent, and an excipient. Colorants and fragrances may additionally be included. In some embodiments, the formulation further includes one or more of the following: amino acids, peptides, phospholipids, additional vitamins, growth factors, and additional anti-aging compounds. Surfactants, gelling agents, and pH balancers may also be included.

In several embodiments, the formulation comprises a combination of various combination groups and individual ingredients. In some embodiments, the formulation comprises, consists essentially of or consists of several or all of the following groups of ingredients:

TABLE 6

| Group | Agent/Ingredient |
|---|---|
| 6.1 | cyclopentasiloxane, dimethicone crosspolymer, dimethicone/vinyl dimethicone crosspolymer, and dimethiconol; |
| 6.2 | titanium dioxide, caprylic/capric triglyceride, alumina, silica, and polyhydroxy stearic acid; |
| 6.3 | zinc oxide, caprylic/capric triglyceride, jojoba esters, and glyceryl behenate/eicosadioate; |
| 6.4 | bisabolol and Zingiber Officinale (ginger) root extract; |
| 6.5 | Magnolia Officinalis bark extract and caprylic/capric triglyceride; |
| 6.6 | caprylic/capric triglyceride and Crithmum maritimum extract; |
| 6.7 | iron oxides (e.g., Cl 77492) and triethoxycaprylylsilane; |
| 6.8 | iron oxides (e.g., Cl 77491) and triethoxycaprylylsilane; |
| 6.9 | chromium oxide greens (e.g., Cl 77288); |
| 6.10 | iron oxides (e.g., Cl 77499) and triethoxycaprylylsilane; |
| 6.11 | water; |
| 6.12 | niacinamide; |
| 6.13 | magnesium carboxymethyl beta-glucan; |
| 6.14 | phenoxyethanol and ethylhexylglycerin; |
| 6.15 | disodium lauriminodipropionate tocopheryl phosphate; |
| 6.16 | cyclopentasiloxane, disteardimonium hectorite, and propylene carbonate. |

In several embodiments, effective (e.g., therapeutic) amounts of active ingredients are provided in the formulation. In many embodiments, the percentages provided are % m/m or % w/w.

In one embodiment, group (6.1) above is provided in a range of about 30-80% (e.g., 30%, 50%, 60%, 70%, 80% and ranges in between) of the total formulation, with individual ranges (with respect to percentage amount vis-à-vis the select group of the following ingredients) as follows: cyclopentasiloxane (about 30%, 45%, 50%, 70%, 75% 80%, 82%, 83%, 85%, 90%, and ranges in between), dimethicone crosspolymer (about 6%, 8%, 10%, 12%, 14%, 20%, and ranges in between), dimethicone/vinyl dimethicone crosspolymer (about 1%, 2%, 3%, 6%, 10%, and ranges in between) and dimethiconol (about 0.01%, 0.05%, 0.075%, 0.1%, 0.5%, 1%, 2%, 5%, and ranges in between). By way of example, if cyclopentasiloxane is provided at 80% vis-à-vis the select group of compounds listed in group (6.1), and group (6.1) is provided as 60% of the total formulation, then cyclopentasiloxane will be present as 48% of the total formulation. In several embodiments, group (6.1) can further include or be substituted with elastomers, such as high molecular weight silicone elastomers, decamethylcyclopentasiloxane, phenyl silicons, alkylmethylsiloxanes, polydimethylsiloxanes, cross-linked silicone elastomer dispersions, hexamethyldisolixane, cyclomethicone, and trimethylsilyamodimethicone, and combinations thereof. In several embodiments, group (6.1) can be a gel and be used in conditioning the skin, as well as for sebum absorption.

In one embodiment, group (6.2) and group (6.3) above are provided in a range of about 15-30% (e.g., 15%, 18%, 20%, 23%, 25%, 28%, 30%, and ranges in between) of the total formulation for group (6.2) and 5-20% (e.g., 5%, 8%, 10%, 12%, 15%, 18%, 20%, and ranges in between) of the total formulation for group (6.3). Individual ranges (with respect to percentage amount vis-à-vis the select group of the following ingredients) can be as follows for group (6.2): titanium dioxide (about 20%, 30%, 40%, 50%, 60%, 70%, and ranges in between), caprylic/capric triglyceride (about 20%, 35%, 40%, 42%, 44%, 46%, 50%, 55%, 65%, 75%, and ranges in between), alumina (about 0.5%, 1%, 1.5%, 2%, 2.25%, 2.5%, 2.75%, 3%, 4%, 5%, 8%, and ranges in between), silica (about 0.5%, 1%, 1.5%, 2%, 2.5%, 3%, 4%, 5%, 8%, and ranges in between) and polyhydroxy stearic acid (about 0.5%, 0.75% 1%, 1.25%, 1.5%, 1.75%, 2%, 5%, and ranges in between). Individual ranges (with respect to percentage amount vis-à-vis the select group of the following ingredients) can be as follows for group (6.3): zinc oxide (50%, 60%, 65%, 70%, 75%, 80, 95, and ranges in between), caprylic/capric triglyceride (about 10%, 15%, 20%, 25%, 30%, 35%, 45%, 50% and ranges in between), jojoba esters or jojoba-based compounds (about 0.5%, 1%, 1.5%, 2%, 2.5%, 3%, 4%, 5%, and ranges in between), and glyceryl behenate/eicosadioate (about 0.5%, 1%, 1.5%, 2%, 3%, 4%, 5%, and ranges in between).

According to several embodiments, zinc oxide and titanium dioxide are used for UV absorption. Micronized and/or nanoscale zinc oxide together with titanium dioxide can be used and can provide strong protection against ultraviolet radiation and can be used in sunscreen, sunblock, tanning, and sun tanning lotions, creams, gels, and liquids according to several embodiments. Titanium dioxide can also be used herein as a pigment, sunscreen, sunblock and a thickener. Other ingredients that can be used in addition to or as a substitute for the ingredients in group (6.2) or (6.3) include but are not limited to, 4-methylbenzylidene camphor (Enzacamene, Parsol 5000, Eusolex 6300, MBC), Tinosorb M (bisoctrizole, methylene bis-benzotriazolyl tetramethylbutylphenol, MBBT), Tinosorb S (Bis-ethylhexyloxyphenol methoxyphenol triazine, bemotrizinol, BEMT, anisotriazine), Meroyl XL, (drometrizole trisiloxane), Benzophenone-9 (Uvinul DS 49, CAS 3121-60-6, Sodium Dihydroxy Dimethoxy Disulfobenzophenone), Uvinul T 150 (Octyl triazone, ethylhexyl triazone, EHT), Uvinul A Plus (Diethylamino Hydroxybenzoyl Hexyl Benzoate), Uvasorb HEB (Iscotrizinol, Diethylhexyl butamido triazone, DBT), Parsol SLX (Dimethico-diethylbenzalmalonate, Polysilicone-15), and Isopentenyl-4-methoxycinnamate (Isoamyl p-Methoxycinnamate, IMC, Neo Heliopan E1000, Amiloxate). In some embodiments, the formulations comprise 5-15% zinc oxide and 7-15% titanium dioxide.

In one embodiment, group (6.4) above is provided in a range of about 0.05-2% of the total formulation (e.g., 0.05%, 0.075%, 0.1%, 0.125%, 0.15%, 0.175%, 0.2%, 0.25%, 0.3%, 0.5%, 0.75%, 1%, 1.5%, 2%, and ranges in between), with individual ranges (with respect to percentage amount vis-à-vis the select group of the following ingredients) as follows: bisabolol (about 75%, 80%, 85%, 90%, 95%, 97%, 98%, 99%, 99.5%, and ranges in between) and *Zingiber Officinale* root extract (about 0.05%, 0.075%, 0.1%, 0.125%, 0.15%, 0.175%, 0.2%, 0.25%, 0.3%, 0.5%, 0.75%, 1%, 1.5%, 2%, and ranges in between). In several embodiments, fragrances can be used, including lavender, lemon, orange, *gardenia*, jasmine, mint, and other flower and fruit extracts. Fragrance-free alternatives are also used herein.

In one embodiment, group (6.5) above is provided in a range of about 0.05-2% of the total formulation (e.g., 0.05%, 0.075%, 0.1%, 0.2%, 0.3%, 0.4%, 0.5%, 0.6%, 0.7%, 0.8%, 0.9%, 1%, 1.25%, 1.5%, 1.75%, 2%, and ranges in between), with individual ranges (with respect to percentage amount vis-à-vis the select group of the following ingredients) as follows: *Magnolia Officinalis* bark extract (about 0.05%, 0.075%, 0.1%, 0.125%, 0.15%, 0.175%, 0.2%, 0.25%, 0.3%, 0.5%, 0.75%, 1%, 1.5%, 2%, and ranges in between) and caprylic/capric triglyceride (about 75%, 80%, 85%, 90%, 95%, 97%, 98%, 99%, 99.5%, 99.6%, 99.7%, 99.8%, 99.9%, and ranges in between).

In one embodiment, group (6.6) above is provided in a range of about 0.1-5% of the total formulation (e.g., 0.1%, 0.5%, 1%, 2%, 3%, 4%, 5%, and ranges in between), with individual ranges (with respect to percentage amount vis-à-vis the select group of the following ingredients) as follows: caprylic/capric triglyceride (about 75%, 80%, 85%, 90%, 95%, 97%, 98%, 99%, 99.5%, and ranges in between) and *Crithmum Maritimum* extract (about 0.5%, 1%, 2%, 3%, 4%, 5%, 7%, 10%, 12%, and ranges in between. In some embodiments, fractionated coconut oil can be used in place of, or in addition to caprylic and/or capric triglycerides. Additionally, in some embodiments, synthetic sea fennel extract is used. Alternatively, retinol (e.g., vitamin A—synthetic or natural) may be used in addition to, or in place of, sea fennel extract.

In one embodiment, group (6.7) above is provided in a range of about 0.1-5% of the total formulation (e.g., 0.1%, 0.5%, 1%, 2%, 3%, 4%, 5%, and ranges in between), with individual ranges (with respect to percentage amount vis-à-vis the select group of the following ingredients) as follows: iron oxides, e.g., CI 77492, (about 90%, 95% 98%, 99%, 99.5%, 100%, and ranges in between) and triethoxycaprylylsilane (about 0.1%, 0.3%, 0.5%, 0.75%, 1%, 2%, 3%, 4%, 5%, and ranges in between).

In one embodiment, group (6.8) above is provided in a range of about 0.01-3% of the total formulation (e.g., 0.01%, 0.05%, 0.075%, 0.1%, 0.15%, 0.2%, 0.3%, 0.5%, 0.7%, 1%, 2%, 3%, and ranges in between), with individual ranges (with respect to percentage amount vis-à-vis the select group of the following ingredients) as follows: iron oxides, e.g., CI 77491, (about 90%, 95% 98%, 99%, 99.5%, 100%, and ranges in between) and triethoxycaprylylsilane (about 0.1%, 0.3%, 0.5%, 0.75%, 1%, 2%, 3%, 4%, 5%, and ranges in between).

In one embodiment, ingredient (6.9) above, chromium oxide greens, is provided in a range of about 0.1-5% (e.g., 0.1%, 0.25%, 0.5%, 0.6%, 0.75%, 1%, 2%, 3%, 4%, 5%, and ranges in between) of the total formulation. Alternatively, hydrated chromium oxide, hydrated chromium green, and/or chromium cobalt aluminum oxide is used. In several embodiments, other green pigments are used, for example green tea extract, Ultramarines (CI 77007), and the like.

In one embodiment, group (6.10) above is provided in a range of about 0.001-5% of the total formulation (e.g., 0.001%, 0.005%, 0.01%, 0.05%, 0.1%, 0.5%, 1%, 2%, 3%, 4%, 5%, and ranges in between), with individual ranges (with respect to percentage amount vis-à-vis the select group of the following ingredients) as follows: iron oxides, e.g., CI 77499, (about 90%, 95% 98%, 100%, and ranges in between) and triethoxycaprylylsilane (about 1%, 2%, 3%, 4%, 5%, and ranges in between). In several embodiments, the formulation is free of one or more members of group (6.10).

In one embodiment, ingredient (6.11) above, water (e.g., distilled and/or deionized water), is provided in a range of about 1-10% (e.g., 1%, 2%, 3%, 4%, 5%, 6%, 7%, 8%, 9%, 10%, and ranges in between) of the total formulation. Alternatively, isocetyl stearoyl stearate is used instead or in addition to water in a range of about 5-20% (1-10% (e.g., 1%, 2%, 3%, 4%, 5%, 6%, 7%, 8%, 9%, 10%, and ranges in between).

In one embodiment, ingredient (6.12) above, niacinamide, is provided in a range of about 0.01-5% of the total formulation (e.g., 0.01% 0.1%, 0.5%, 0.75%, 1%, 2%, 3%, 4%, 5%, 10%, and ranges in between) of the total formulation.

Additionally, other components of the vitamin B complex group or other vitamin B based compounds can be used in addition to, or in place of, niacinamide (also called nicotinamide). Additionally, other agents that complex with one or more of nicotinamide adenine dinucleotide (NAD) and/or nicotinamide adenine dinucleotide phosphate coenzymes can also be used in several embodiments.

In one embodiment, ingredient (6.13) above is provided in a range of about 0.01-3% of the total formulation (e.g., 0.01%, 0.05%, 0.075%, 0.1%, 0.15%, 0.2%, 0.3%, 0.5%, 0.7%, 1%, 2%, 3%, and ranges in between), with individual ranges (with respect to percentage amount vis-à-vis the select group of the following ingredients) as follows: magnesium carboxymethyl beta-glucan (about 75%, 80%, 85%, 90%, 95% 98%, and ranges in between), glycolic acid (about 0.05%, 0.1%, 0.3%, 0.5%, 0.7%, 1%, 2%, 3%, and ranges in between), chloracetic acid (about 0.01%, 0.025%, 0.05%, 0.075%, 0.1%, 0.2%, 0.5%, 1%, and ranges in between), and water (about 2%, 4%, 6%, 8%, 10%, and ranges in between).

In one embodiment, group (6.14) above is provided in a range of about 0.01-3% of the total formulation (e.g., 0.01%, 0.05%, 0.075%, 0.1%, 0.15%, 0.2%, 0.3%, 0.5%, 0.7%, 1%, 2%, 3%, and ranges in between), with individual ranges (with respect to percentage amount vis-à-vis the select group of the following ingredients) as follows: phenoxyethanol (about 75%, 80%, 85%, 90%, 95% 98%, 100%, and ranges in between), ethylhexlyglycerin (about 2%, 4%, 6%, 8%, 10%, 12%, and ranges in between), and tocopherol (about 0.01%, 0.05%, 0.075%, 0.1%, 0.2%, 0.3%, 0.5%, 1%, 2%, and ranges in between).

In one embodiment, ingredient (6.15) above is provided in a range of about 0.01-7% of the total formulation (e.g., 0.01%, 0.05%, 0.1%, 0.5%, 1%, 1.5%, 2%, 2.5%, 3%, 4%, 5%, 7% and ranges in between), with individual ranges (with respect to percentage amount vis-à-vis the select group of the following ingredients) as follows: disodium lauriminodiapropionate tocopheryl phosphates (about 25%, about 30%, about 35%, about 40%, about 45%, about 50%, and ranges in between), water (about 40%, 50%, 60%, 70%, 75%, 80%, and ranges in between), phenoxyethanol (about 0.2%, 0.4%, 0.6%, 0.8%, 1%, 2%, 4% and ranges in between), benzoic acid (about 0.05%, 0.075%, 0.1%, 0.15%, 0.2%, 0.4%, 0.6%, and ranges in between), and dehydroacetic acid (about 0.02%, 0.04%, 0.06%, 0.08%, 0.1%, 0.2%, 0.5%, and ranges in between).

In one embodiment, group (6.16) above is provided in a range of about 1% to about 25% of the total formulation (e.g., 1%, 3%, 5%, 10%, 15%, 20%, 25%, and ranges in between), with individual ranges (with respect to percentage amount vis-à-vis the select group of the following ingredients) as follows: cyclopentasoiloxane (about 65%, 70%, 75%, 80%, 85%, 90%, 95%, 98%, and ranges in between), disteardimonium hectorite (about 5%, 8%, 12%, 15%, 18%, 20%, and ranges in between), and propylene carbonate (about 2%, 3%, 4%, 5%, 6%, 7%, 9%, and ranges in between).

In one embodiment, the formulation comprises or consists essentially of some or all of the following agents:

TABLE 7

| Agent/Ingredient | Approximate % Amount in Formulation |
|---|---|
| Siloxane (e.g., Cyclopentasiloxane) | 30-60% |
| Caprylic/capric triglyceride | 5-20% |

TABLE 7-continued

| Agent/Ingredient | Approximate % Amount in Formulation |
|---|---|
| Titanium Dioxide | 5-15% |
| Zinc Oxide | 2-15% |
| Dimethicone Crosspolymer | 2-10% |
| Water | 2-10% |
| Niacinamide | 0.5-5% |
| Disteardimonium hectorite | 0.5-5% |
| Dimethicone/vinyl dimethicone crosspolymer | 0.5-5% |
| Iron oxides | 0.5-5% |
| Vitamin E Compound (e.g., Disodium Lauriminodipropionate Tocopheryl Phosphates) | 0.1-5% |
| Alumina | 0.1-5% |
| Chromium oxide green | 0.1-5% |
| Propylene carbonate | 0.1-5% |
| Silica | 0.05-5% |
| Dimethiconol | 0.05-5% |
| Jojoba esters | 0.05-5% |
| Polyhydroxysteric acid | 0.05-5% |
| Bisabolol | 0.05-5% |
| Glyceryl behenate | 0.05-5% |
| Phenoxyethanol | 0.05-5% |
| Magnesium carboxymethyl beta-glucan | 0.05-5% |
| Chrithmum maritimum extract | 0.05-5% |
| Triethoxycaprylylsilane | 0.005-5% |
| Ethylhexylglycerin | 0.005-5% |
| Magnolia officinale bark extract | 0.001-5% |
| Benzoic acid | 0.001-5% |
| Zingiber officinale (ginger) root extract | 0.001-5% |
| Dehydroacetic acid | 0.0001-5% |
| Tocopherol | 0.0001-5% |
| Chloracetic acid | 0.00001-5% |

The percentages provided above for Tables 6 and 7 are provided as % m/m or % w/w in some embodiments. In other embodiments, these ingredients are provided as % m/v, % v/v, % m/w, or % w/v. In several embodiments, a therapeutic or effective amount of each therapeutic ingredient is included in the formulation. A therapeutic or effective amount may be that which reduces irritation, reduces redness, reduces inflammation, mediates an immune response, or soothes the skin.

In some embodiments, one or more of the groups of ingredients may be, but not necessarily, obtained as Dow Corning 9546 or 9548 Elastomer Blend, GCP55TEL, GC70MZCJ-G, SymRelief 100, MAXnolia O, Native Essence, Unipure Yellow, Unipure Red, Chromium Oxide Green, Niacinamide PC, CM-Glucan Forte, Euxyl PE 9010, Vital ET, and Bentone Gel VS-5 PC V HV. Some embodiments employ Unipure Black, although several embodiments are free of Unipure Black.

In one embodiment, a thickener or viscosity increasing agent is provided in a range of about 0.1-15% of the total formulation (e.g., 0.1%, 0.5%, 1%, 2%, 3%, 4%, 5%, 10%, 12%, 15%, and ranges in between). The thickener can optionally include methylcellulose in alternate embodiments. The percentages are provided as % m/m in some embodiments. In other embodiments, these ingredients are provided as % w/w, % m/v, % v/v, % m/w, or % w/v.

In several embodiments, the formulation can have an SPF between 5 SPF and 100 SPF. In some embodiments, the topical composition can have an SPF of 15, 20, 25, 30, 35, 40, 45, 50, 60, 70, 80, 90, 100, and ranges in between. Greater SPF values may also be used in some embodiments. A physical sunscreen with an SPF of 50 is provided in several embodiments.

In several embodiments, the formulation comprises a stabilizer, suspending agent and/or thickener. Dimethicone crosspolymer is a silicon derivative that can be used herein as a stabilizing or a suspending agent or a thickener. Types of dimethicone crosspolymers that can be used as a stabilizing agent, suspending agent or a thickener include, but are not limited to, silicone CS-1600, which is a mixture between dimethicone crosspolymer and cyclopentasiloxane, dimethicone crosspolymer 3, dimethicone crosspolymer PEG-8, cetyl dimethicone/dimethicone cross polymer, and dimethicone/vinyl dimethicone crosspolymer, and combinations thereof.

In several embodiments, a dispersing agent is used in order to achieve a more even distribution (and stabilization, in several embodiments) of solid particles, like pigments and fillers, throughout the formulation. In several embodiments, disteardimonium hectorite, a derivative of the naturally occurring clay mineral hectorite is used, either alone or in conjunction with other agents. Disteardimonium hectorite is generated by replacement of a portion of the sodium cations of hectorite clay with stearyldimonium groups, which include 18 carbon chains. Disteardimonium hectorite is a quaternary ammonium compound, and other compounds of this class can be used, in several embodiments, in addition to or in place of disteardimonium hectorite. In some embodiments, the quaternary ammonium compounds are synthetic, though naturally occurring compounds may also be used. For example, other quaternary ammonium compounds that can be used include, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, and domiphen bromide, or combinations of two or more thereof.

In several embodiments described herein, the topical formulation comprises *zingiber officinale* extract to beneficially affect skin condition (e.g., smoothness, reduced irritation, increased barrier function, etc.). *Zingiber officinale* extract can be combined with various oils, other extracts, and/or vitamin compositions, in several embodiments. For example, *Glycyrrhiza Glabra* (licorice) extract, mulberry extract, *Sanguisorba Officinalis* (Great Burnet) extract, *Rhodiola rosea* extract, *Angelica Arcangelica* extract, and the like may be used, alone or in combination with *zingiber officinale* extract (or with other components described herein). Tocopherol is a vitamin E compound, with benefits described herein.

*Zingiber officinale* extract combined with bisabolol (synthetic or natural) works synergistically in several embodiments to enhance the skin calming, anti-redness and anti-irritant effects. In some embodiments, the ratio of *Zingiber officinale* and bisabolol is 100:1, 99:1; 90:1; 75:1, 50:1, 25:1, 10:1 and ranges in between. In some embodiments, the ratio of the bisabolol and *Zingiber officinale* is 100:1, 99:1; 90:1; 75:1, 50:1, 25:1, 10:1, and ranges in between. In one embodiment, the two agents when combined work synergistically as anti-irritant agents, and further when combined with vitamin E compounds and/or niacinimide (e.g., 1-5%) provide enhanced synergy with anti-irritant (e.g., anti-inflammatory) effects. Additionally, when combined with a high SPF (such as SPF 30, 50 or more), the formulations' anti-irritant and anti-redness effects on skin are further pronounced as the SPF formulation reduces further damage/irritation to the skin.

In several embodiments, the *zingiber officinale* and/or bisabolol (synthetic or natural) is combined with *Magnolia officinalis* extract, which functions as a skin conditioning agent, and has antimicrobial properties. In several embodiments, the ratio of *Magnolia officinalis* extract to *zingiber officinale* and/or bisabolol is 50:1, 40:1, 30:1, 25:1:20:1, 10:1, 5:1, 2:1 and ranges in between. In several embodiments, the *zingeber officinale*, bisabolol, and/or *Magnolia officinalis* is combined with *chrithmum maritimum* extract, which functions as a skin conditioning agent. In several embodiments, the ratio of *Magnolia officinalis* extract to *zingiber officinale*, bisabolol, and/or *Magnolia officinalis* is 1:10, 1:25, 1:50, 1:75, 1:100, 1:250, 1:500, 500:1, 250:1, 100:1, 75:1, 50:1, 25:1, 10:1 and ranges in between. In several embodiments, these combinations exhibit synergistic anti-irritant and/or anti-redness effects. In several embodiments, these combinations promote smoother, more hydrated skin that, in turn, reduces future irritation and redness.

As described herein, anti-inflammatory agents other than vitamin E compounds can be used in addition to, or in lieu of, vitamin E compounds. Anti-inflammatory agents are used, in some embodiments, to inhibit the inflammatory pathway. For example, during the inflammatory process in the epidermal layer, inflammatory mediators (such as cytokines, chemokines, prostanoids such as prostaglandins, reactive oxygen species, etc.) may be released. In several embodiments, the vitamin E compounds are used to assist in reduction of effects caused by UV exposure, such as UVA or UVA exposure. In several embodiments, the vitamin E compounds help prevent the formation of sunburn on cells (e.g., epidermal cells). Also associated with this effect, in one embodiment, is the protection or reduction in the UV induced depletion or alteration of epidermal Langerhans cells, the depletion of which is associated with immunosuppression (which can exacerbate heightened skin sensitivity). In several embodiments, the vitamin E compounds also aid in reducing redness or other skin discoloration. An anti-inflammatory agent, as used herein in several embodiments, interrupts (e.g., or otherwise inhibits) this pathway, which in turn helps to reduce inflammation. In some embodiments, the balancing of inflammation and inflammatory pathways is accomplished. In one embodiment, melanin production may also be beneficially affected.

In several embodiments, the invention comprises or consists essentially of cyclopentasiloxane, dimethicone crosspolymer, dimethicone/vinyl dimethicone crosspolymer, caprylic/capric triglyceride, titanium dioxide and/or zinc oxide, disteardimonimum hectorite, propylene carbonate, niacinamide, bisabolol, *Zingiber officinale* extract, *Magnolia officinalis* bark extract, *Crithmum maritimum* extract, disodium lauriminodipropionate tocopheryl phosphates, phenoxyethanol, benzoic acid, dehydroacetic acid, iron oxides (e.g., CI 77491, CI 77492) and chromium oxide green (e.g., CI 77288).

In several embodiments, the invention comprises or consists essentially of cyclopentasiloxane, caprylic/capric triglyceride, water/aqua/eau, dimethicone crosspolymer, niacinamide, disteardimonium hectorite, dimethicone/vinyl dimethicone crosspolymer, propylene carbonate, disodium lauriminodipropionate tocopheryl phosphates, *Crithmum maritimum* extract, *Magnolia officinalis* bark extract, *Zingiber officinale* (ginger) root extract, magnesium carboxymethyl, beta-glucan, jojoba esters or derivatives, bisabolol, silica, polyhydroxystearic acid, dimethiconol, alumina, glyceryl behenate/eicosadioate, phenoxyethanol, triethoxycaprylylsilane, ethylhexylglycerin, tocopherol, dehydroacetic acid, benzoic Acid, glycolic Acid, chloroacetic acid, chromium oxide greens (e.g., CI 77288), iron oxides (e.g., CI 77491, CI 77492, CI 77499). In several embodiments, the above compounds are supplemented with one or more sunscreen ingredients.

In several embodiments, the invention comprises or consists essentially of cyclopentasiloxane, caprylic/capric triglyceride, titanium dioxide, zinc oxide, water/aqua/eau, dimethicone crosspolymer, niacinamide, disteardimonium hectorite, dimethicone/vinyl dimethicone crosspolymer, propylene carbonate, disodium lauriminodipropionate tocopheryl phosphates, *Crithmum maritimum* extract, *Magnolia officinalis* bark extract, *Zingiber officinale* (ginger) root extract, magnesium carboxymethyl beta-glucan, jojoba esters, bisabolol, silica, polyhydroxystearic acid, dimethiconol, alumina, glyceryl behenate/eicosadioate, phenoxyethanol, triethoxycaprylylsilane, ethylhexylglycerin, tocopherol, dehydroacetic acid, benzoic acid, glycolic acid, chloroacetic acid, [+/−CI 77288, CI 77491, CI 77492, CI 77499).

In several embodiments, the invention comprises or consists essentially of cyclopentasiloxane, dimethicone crosspolymer, dimethicone/vinyl dimethicone crosspolymer, dimethiconol, caprylic/capric triglyceride, alumina, silica, polyhydroxysteric acid, jojoba esters, glyceryl behenate/eicosadioate, water, phenoxyethanol, benzoic acid, dehydroacetic acid, glycolic acid, choloracetic acid, ethylhexylglycerin, tocopherol, disteardimonium hectorite, triethoxycaprylylsilane, iron oxides (e.g., CI 77491, CI 77492), chromium oxide greens (e.g., CI 77288) and two or more of bisabolol, *Zingiber officinale, Magnolia officinalis* bark extract, *crithmum maritimum* extract, disodium lauriminodiapropionate tocopheryl phosphates, titanium dioxide, zinc oxide, niacinamide, and magnesium carboxymethyl beta-glucan.

The topical formulations described herein may be used as a primer, foundation, concealer or general skin care product. Facial lotion and eye creams are provided in some embodiments.

According to several embodiments, the ingredients may be delivered in a single formulation or separately. For example, a skin care/conditioning agent and an anti-inflammatory agent and sunscreen can be in a single formulation. Alternatively, the ingredients or groups of ingredients may be provided in separate compositions. For example, the anti-inflammatory agent(s) may be in one formulation and the sunscreen in another. The topical formulations are, according to several embodiments, applied once a day, twice a day, or every other day. Greater frequencies may also be used. Lesser frequencies may also be used, for example in maintenance phase after the desired effects have been achieved. Multi-chamber dispensers can be used in some embodiments. In several embodiments, a kit comprising a formulation as described herein is provided along with instructions for use. In one embodiment, the kit further comprises a separate sunscreen to be reapplied on a more frequent basis (such sunscreen can be provided as a brush on sunscreen). Applicators (brushes, sticks, sponges, etc.) may be provided to apply the formulations described herein, and may also be included in a kit. The kit can comprise one or more of the formulations described herein in varying strengths (e.g., of the therapeutic ingredients).

In several embodiments, skin irritation is reduced by 10-100% after use. For example, significant skin calming effects and improvements in overall appearance, radiance, skin health, skin smoothness, and/or skin tone (evenness, e.g., lack of redness) are visible in several embodiments after 4 weeks, 8 weeks and 12 weeks. Certain improvements in skin may be visible or felt upon use or within days of use. Although specific regions of skin irritation or redness are treated according to several embodiments, an overall skin rejuvenating effect can also be achieved on skin that has no identifiable regions of irritation.

Several embodiments of the formulations are particularly advantageous because they provide coverage (e.g., color, camouflage) in a formulation that goes on smoothly and is not chalky or sticky. This is helpful to cover areas of redness or irritation while the formulation is simultaneously working to reduce said redness or irritation. This is also helpful to minimize the number of products a user applies to his/her face (or body) because it reduces the need for a separate foundation. A beige formulation with green undertones is provided to counteract redness in some embodiments. A non-fragranced clear formulation is provided in other embodiments.

Several embodiments of the formulations are water resistant. In one embodiment, the formulation is water resistant, e.g., with respect to SPF, for up to 30, 40, 60 and 120 minutes. Long-wear formulations are provided in several embodiments.

The formulations, according to several embodiments, are especially effective because they offer a multi-modal approach to reduction of redness or irritation. The combination of the skin conditioning agent with the anti-inflammatory and sunscreen provides a multi-modal approach that addresses discoloration via multiple pathways and results in the creation of a unique and effective formulation. In several embodiments, the anti-inflammatory agents, by acting through a pathway that involves inflammation's role in irritation, are particularly effective when combined with the skin conditioning and/or antimicrobial agents.

In some embodiments, one or more mild keratolytic agents may be optionally included, wherein the keratolytic is gentle enough to be used on sensitive skin that is, for example, irritated, inflamed, and red. Mild keratolytic agents may help remove or soften older, damaged surface tissue (e.g., keratin) and promote the generation of new skin cells. Mild keratolytic agents used in the formulations described herein include but are not limited to one or more of the following: plant extracts (such as from the aster family), salicylic acid, alpha hydroxy acid, beta hydroxy acid, sulfur, azelaic acid, glycolic acid, urea, lactic acid, resorcinol, allantoin, fruit acids, and fruit oils. Gentle exfoliants include chemical or mechanical exfoliants. The keratolytic agents are provided, in several embodiments, in a range of about 0.005% to about 10% (e.g., 0.005%, 0.05%, 0.1%, 0.5%, 1%, 5%, 10%, and ranges in between).

Skin Care Formulations as Described Generally Herein

Several of the ingredients below may be applicable to the formulations described herein for skin renewal (e.g., eye region), treating hyperpigmentation, and/or soothing redness correction.

In those embodiments in which glyceryl behenate is provided, this ingredient behenate may be used, for example, as a skin conditioning agent and/or emollient. In several embodiments described herein, the formulations comprise a glyceryl monoester. Glyceryl compounds that can be used herein instead of or in addition to glyceryl behenate include but are not limited to, glyceryl laurate, glyceryl laurate, glyceryl laurate/oleate, glyceryl adipate, glyceryl alginate, glyceryl arachidate, glyceryl caprate, glyceryl caprylate, glyceryl caprylate/caprate, glyceryl citrate/lactate/linoleate/oleate, glyceryl cocoate, glyceryl collagenate, glyceryl erucate, glyceryl hydrogenated rosinate, glyceryl hydrogenated soyate, glyceryl hydroxystearate, glyceryl isopalmitate, glyceryl isostearate, glyceryl isostearate/myristate, glyceryl isostearates, glyceryl lanolate, glyceryl linoleate, glyceryl linolenate, glyceryl montanate, glyceryl myristate, glyceryl isotridecanoate/stearate/adipate, glyceryl oleate, glyceryl oleate/elaidate, glyceryl palmitate, glyceryl palmitate/stearate, glyceryl palmitoleate, glyceryl pentadecanoate, glyceryl polyacrylate, glyceryl rosinate, glyceryl sesquioleate, glyceryl/sorbitol oleate/hydroxystearate, glyceryl stearate/acetate, glyceryl stearate/maleate, glyceryl tallowate, glyceryl thiopropionate, and glyceryl undecylenate.

In those embodiments in which polyhydroxystearic acid is provided, this ingredient may be used, for example, as a suspending agent and/or an emulsifier that is used to stabilize products in some embodiments. It can be used herein to suspend SPF protection or other components in lotions, liquids, gels, etc.

In those embodiments in which cyclopentasiloxane is provided, this ingredient may be used, for example, as a silicone fluid that can work as an emollient for the skin. Depending on the embodiment, other silicone compounds may be used. For example, other examples of siloxane polymers that can be used herein (instead of or in addition to cyclopentasiloxane) include silica silylate, silica dimethyl silylate, polytrimethylsiloxymethacrylate copolymer, isododecane, acrylates and trifluoropropyldimethyl/trimethylsioxysicate. In some embodiments, these are insoluble in water and used for film forming, wear and water resistance. In several embodiments described herein, the formulation comprises a siloxane polymer. In several embodiments, silicones, including but not limited to cyclopentasiloxane, provide one or more of the following benefits, non-tacky, smooth feel, no oily after-feel, enhanced comfort during use, skin protection from particulate pollution, sebum absorption, enhanced durability of formulations, including increased color uniformity, improved wash-off resistance and duration of usability (e.g., for long-wear formulations). In some cases, where siloxanes are included such as cyclopentasiloxane, a by-product (such as cyclotetrasiloxane in one embodiment) may be present at, for example, 0.1%, 0.5%, 1%, 2%, 5%, and ranges in between.

In those embodiments in which caprylic/capric triglycerides are provided, they may be used, for example, as skin conditioners and/or occlusive agents, the latter serving, in several embodiments, to increase the hydration of the skin (e.g., by preventing loss of moisture through the skin), thereby reducing the tendency of dry skin to become irritated. In some embodiments, caprylic/capric triglycerides are a mixed triester derived from coconut oil and glycerin. Caprylic/capric triglycerides function as a skin conditioning agent in several embodiments, helping to soften, smooth, and/or improve water barrier functions of skin. In several embodiments, they also function as emollient, dispersing agent and/or solvents. In several embodiments, the triglycerides provide a non-greasy barrier as well as skin lubrication. In several embodiments, their use can enhance delivery of ingredients contained in the formulations disclosed herein.

Preservatives such as benzoic acid (and its salt sodium benzoate), dehydroacetic acid, potassium sorbate and/or phenoxyethanol (and others) are used in many embodiments. In some embodiments, these preservatives are in amounts and/or are specifically chosen to be suitable for delicate or sensitive skin. Preservatives can be naturally occurring, modified, or synthetically produced. In addition to, or in lieu of the preservatives recited herein, the following may be used: fermented radish root, rosemary oleoresin extract, salicylic acid, sorbic acid (hexa-2,4-dienoic acid), biphenyl-2-ol (o-phenylphenol), zinc pyrithione, inorganic sulphites, hydrogensulphites, chlorobutanol, 4-hydroxybenzoic acid, 3-acetyl-6-methylpyran-2,4 (3h)-dione (dehydroacetic acid) and its salts, formic acid and its sodium salt, 3,3'-dibromo-4,4'-hexamethylenedioxydibenzamidine (dibromohexamidine) and its salts (including isethionate), thiomersal (inn), phenylmercuric salts (including borate), undec-10-enoic acid and salts, hexetidine, 5-bromo-5-nitro-1,3 dioxane, bronopol, 2,4-dichlorobenzyl alcohol, triclocarban, 4-chloro-m-cresol, triclosan, 4-chloro-3,5-xylenol, 3,3'-bis(1-hydroxymethyl-2,5-dioxoimidazolidin-4-yl)-1, 1'-methylenediurea, poly(1-hexamethylenebiguanide hydrochloride), 2-phenoxyethanol, hexamethylenetetramine (methenamine), methenamine 3-chloroallylochloride, 1-(4-chlorophenoxy)-1-(imidazol-1-yl) 3,3-dimethylbutan-2-one, 1,3-bis(hydroxymethyl)-5,5-dimethylimidazolidine-2, 4-dione, benzyl alcohol, 1-hydroxy-4-methyl-6(2,4,4-trimethylpentyl)-2-pyridon, 6,6-dibromo-4,4-dichloro-2,2'-methylenediphenol: bromochlorophen, 4-isopropyl-m-cresol, mixture of 5-chloro-2-methyl-isothiazol-3(2h)-one and 2-methylisothiazol-3(2h)-one with magnesium chloride and magnesium nitrate, 2 benzyl-4-chlorophenol, 2-chloro-acetamide, chlorhexidine (inn) and its digluconate, diacetate and dihydrochloride, 1-phenoxypropan-2-ol, alkyl (c12-c22) trimethyl ammonium, bromide and chloride, 4,4-dimethyl-1,3-oxazolidine, n-(hydroxymethyl)-n-(dihydroxymethyl-1,3-dioxo-2,5-imidazolinidyl-4)-n'-(hydroxymethyl) urea, 1,6-di(4-amidinophenoxy)-n-hexane (hexamidine) and its salts (including isethionate and p-hydroxy-benzoate, glutaraldehyde (pentane-1,5-dial), 5-ethyl-3,7-dioxa-1-azabicyclo [3.3.0] octane, 3-(p-chlorophenoxy)-propane-1,2-diol (chlorphenesin), sodium hydroxymethylamino acetate (sodium hydroxymethylglycinate), silver chloride (e.g., deposited on titanium dioxide), benzethonium chloride, benzalkonium chloride, bromide and saccharinate, benzylhemiformal, iodopropynyl butyl-carbamate, 3-iodo-2-propynylbutylcarbamate, methylisothiazolinone, and combinations thereof. Antimicrobial preservatives are provided in several embodiments. Anti-fungal and/or anti-bacterial properties may be achieved in several embodiments.

In some embodiments, a formulation described herein is provided in a kit together with other skin care or cosmetic products, along with instructions for use. Methods of making the formulations are provided herein and include, in some embodiments, adding the ingredients to water in a sanitized vessel and mixing until the ingredients are hydrated and uniform. The pH may be adjusted in one embodiment until it reaches about 5.5-7.5 (e.g., 6-7) at 25 degrees Celsius. Several embodiments use extracts, which may be obtained, for example, by the technique of extraction or by in vitro plant cell culture. Extraction includes, but is not limited to, reflux extraction, steeping, decoction, lixiviation, maceration, supercritical fluid extraction, sonication, microwave/ultrasound extraction, solid-phase micro-extraction, pressurized-liquid extraction, solid-phase extraction, and/or surfactant-mediated techniques. Extraction solvents include but are not limited to: water, alcohols, and fats/oils. Examples include but are not limited to water, propylene glycol, polyethylene glycol, butylene glycol, glycerin, glycerides, diglycol ethers, diglycols, and combinations thereof. Components may be isolated and/or purified before or after extraction in some embodiments.

Where percentages are provided for agents, ingredients and compounds, they can be % m/m, % m/w, % w/w, % m/v, % v/v and variations thereof with respect to the formulation as a whole, unless otherwise indicated.

The use of agents, ingredients and compounds may be used interchangeably herein. In several embodiments, reference to the term "based" includes the recited agent, ingredient or compounds. For example, a vitamin E-based compound includes vitamin E itself. As used herein, the terms composition and formulation can be used interchangeably. Salt forms of the acids identified herein may be used instead of or in addition to the acid.

With respect to the use of plural and/or singular terms herein, those having skill in the art can translate from the plural to the singular and/or from the singular to the plural as is appropriate to the context and/or application.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. For example, "an" agent can include one, two or several ingredients (and not necessarily a single ingredient). In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and sub-ranges and combinations of sub-ranges thereof. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth. The phrases "and ranges in between" can include ranges that fall in between the numerical values listed. For example, "1, 2, 3, 10, and ranges in between" can include 1-10, 1-3, 2-10, etc.

While various aspects and embodiments have been disclosed herein, other aspects and embodiments will be apparent to those skilled in the art. The various aspects and embodiments disclosed herein are for purposes of illustration and are not intended to be limiting, with the scope and spirit being indicated by, for example, the following claims.

For the methods disclosed herein, the functions performed in the processes and methods may be implemented in differing order. The disclosure of methods or uses may also include instructing the method or use (for example, in instructions for use).

What is claimed is:

1. A topical skin care formulation, comprising:
   effective amounts of the following ingredients:
   an *Albizia julibrissin* bark extract;
   a *Dunaliella salina* extract;
   a hydrolyzed algin;
   a betaine;
   an *Ascophyllum nodosum* extract;
   an *Asparagopsis armata* extract;
   a *Tremella fuciformis* sporocarp extract;
   at least one of a *Centella asiatica* extract and a *Siegesbeckia orientalis* extract, wherein the *Siegesbeckia orientalis* extract is a darutoside; and
   a preservative, and
   wherein the formulation further comprises water, hydrogenated polyisobutene, cyclopentasiloxane, triglycerides, lauryl polyglyceryl-3 polydimethylsiloxyethyl dimethicone, glycerin, panthenol, mica, dimethicone crosspolymer, sorbitol, jojoba esters, sodium hyaluronate, palmitoyl tripeptide-5, sucrose, pantolactone, tocopherol, sodium chloride, dimethicone crosspolymers, silica, polyhydroxystearic acid, glyceryl behenate eicosadioate, dimethicone, lauroyl lysine, dimethiconol, ethylhexylglycerin, triethoxycaprylylsilane, alumina, and iron oxides.

2. The formulation of claim 1,
   wherein the ingredients are provided collectively in a range of 0.3-10% of the formulation, and
   wherein the formulation further comprises one or more solvents provided in a range of 50-95% of the formulation.

3. The formulation of claim 1, wherein the formulation is free from one or more of the following: parabens, sulfates, phthalates, talc, dyes, mineral oils, and gluten.

4. The formulation according to claim 1, further comprising one or more additional ingredients selected from the group consisting of: sunscreen agents, viscosity agents, surfactants, emulsifiers, fragrances, colorants, and solvents.

5. The formulation of claim 1, wherein the formulation comprises said *Centella asiatica* extract and said *Siegesbeckia orientalis* extract.

6. The formulation of claim 1, wherein said formulation is a cream, lotion or serum effective for reducing the appearance of dark circles and puffiness around the eye region.

7. The formulation of claim 1, further comprising one or more of titanium dioxide and zinc oxide to provide sun protection.

8. The formulation of claim 1, wherein the preservative is selected from the group consisting of phenoxyethanol, potassium sorbate, sodium benzoate, citric acid, and combinations thereof.

9. The formulation of claim 1, further comprising titanium dioxide and zinc oxide collectively in a range of about 5-20% of the formulation to provide a sun protection factor of 15 or more.

10. A topical skin care formulation, comprising:
(i) a combination of *Albizia, Tremella, algin, Ascophyllum*, betaine, *Dunaliella, Asparagopsis*, and a darutoside, said combination in a range of about 0.3-10% of the total formulation,
  wherein said combination is present in an effective amount, and
  wherein said darutoside is extracted from *Siegesbeckia orientalis;*
(ii) one or more preservatives, viscosity agents, and emulsifiers, collectively in a range of about 2-20% of the total formulation, wherein said one or more preservatives are present in an effective amount; and
(iii) one or more solvents in a range of about 30-95% of the total formulation.

11. The formulation of claim 10, further comprising water, siloxanes, triglycerides, dimethicone, glycerin, panthenol, jojoba esters, sodium hyaluronate, palmitoyl tripeptide-5, pantolactone, and tocopherol.

12. The formulation of claim 10, further comprising water, sorbitol, palmitoyl tripeptide-5, panthenol, sodium hyaluronate, sucrose, glycerin, xanthan gum, polysorbate 20, phenoxyethanol, ethylhexylglycerin, caprylyl glycol, and caprylhydroxamic acid.

13. The formulation of claim 10, further comprising sorbitol, xanthan gum, polysorbate 20, caprylyl glycol, and caprylhydroxamic acid.

14. The formulation of claim 10,
wherein the *Albizia* comprises *Albizia Julibrissin* or an extract thereof,
wherein the *Tremella* comprises *Tremella fuciformis* sporocarp or an extract thereof,
wherein the algin comprises hydrolyzed algin,
wherein the *Aseophyllum* comprises *Aseophyllum nodosa* or an extract thereof,
wherein the *Dunaliella* comprises *Dunaliella salina* or an extract thereof, and
wherein the *Asparagopsis* comprises *Asparagopsis armata* or an extract thereof.

15. The formulation of claim 10, further comprising titanium dioxide and zinc oxide collectively in a range of about 5-20% of the formulation to provide a sun protection factor of 15 or more.

16. The formulation of claim 10, wherein the formulation is free from one or more of the following: parabens, sulfates, phthalates, talc, dyes, mineral oils, and gluten.

17. The formulation of claim 10, further comprising an extract from *Centella asiatica*.

18. A topical skin care formulation comprising effective amounts of the following ingredients:
a *Siegesbeckia orientalis* extract;
a *Centella asiatica* extract;
an *Albizia julibrissin* bark extract
a *Dunaliella salina* extract;
a hydrolyzed algin;
a betaine;
an *Ascophyllum nodosum* extract;
an *Asparagopsis armata* extract;
a *Tremella fuciformis* sporocarp extract; and
a preservative.

\* \* \* \* \*